US009856513B2

(12) United States Patent
Cerf et al.

(10) Patent No.: US 9,856,513 B2
(45) Date of Patent: Jan. 2, 2018

(54) METHODS AND ARRAYS FOR CONTROLLED MANIPULATION OF DNA AND CHROMATIN FRAGMENTS FOR GENETIC AND EPIGENETIC ANALYSIS

(71) Applicant: CORNELL UNIVERSITY, Ithaca, NY (US)

(72) Inventors: Aline Cerf, Toulous (FR); Harold G. Craighead, Ithaca, NY (US); Harvey C. Tian, Fayetteville, AR (US)

(73) Assignee: CORNELL UNIVERSITY, Ithaca, NY (US)

( * ) Notice: Subject to any disclaimer, the term of this patent is extended or adjusted under 35 U.S.C. 154(b) by 343 days.

(21) Appl. No.: 14/374,819

(22) PCT Filed: Jan. 28, 2013

(86) PCT No.: PCT/US2013/023450
§ 371 (c)(1),
(2) Date: Jul. 25, 2014

(87) PCT Pub. No.: WO2013/112999
PCT Pub. Date: Aug. 1, 2013

(65) Prior Publication Data
US 2015/0011425 A1    Jan. 8, 2015

Related U.S. Application Data

(60) Provisional application No. 61/591,606, filed on Jan. 27, 2012, provisional application No. 61/667,491, filed on Jul. 3, 2012.

(51) Int. Cl.
*C12Q 1/68* (2006.01)
*G01N 1/30* (2006.01)

(52) U.S. Cl.
CPC ........ *C12Q 1/6806* (2013.01); *C12Q 1/6837* (2013.01); *G01N 1/30* (2013.01)

(58) Field of Classification Search
None
See application file for complete search history.

(56) References Cited

FOREIGN PATENT DOCUMENTS

WO    WO 2009046445 A1 *  4/2009   .......... C12Q 1/6869
WO       2012/125547 A2    9/2012

OTHER PUBLICATIONS

Heng et al (1992) "High resolution mapping of mammalian genes by in situ hybridization to free chromatin" Proc. Natl. Acad Sci 89:9509-9513.*

(Continued)

*Primary Examiner* — Karen S Weiler
(74) *Attorney, Agent, or Firm* — FisherBroyles, LLP; Andrew K. Gonsalves, Esq.

(57) ABSTRACT

The present invention relates to methods and arrays for use in high resolution imaging of individual nucleic acid molecules and chromatin fragments, including native chromatin fragments. In one aspect, the present invention relates to a chromatin array that includes a transfer platform having a support and a transfer surface layered on the support. The chromatin array also includes a plurality of elongated individual native chromatin fragments coupled to the transfer surface in an orderly pattern suitable for high resolution imaging of the plurality of native chromatin fragments. The native chromatin fragments of the chromatin array include both DNA and histones.

14 Claims, 17 Drawing Sheets
(5 of 17 Drawing Sheet(s) Filed in Color)

(56) References Cited

OTHER PUBLICATIONS

O'Neill et al. (2003) "Immunoprecipation of native chromatin: NChIP." Methods 31(1):76-82.*
Noll et al. (1975) "Preparation of Native Chromatin and Damage Caused by Shearing" Science 187(4182):1203-1206.*
Zaret (1999) "In vivo analysis of chromatin structure" Methods in Enzymology 304:612-626.*
Cerf et al. (2009) "Transfer printing of sub-100nm nanoparticles by soft lithography with solvent mediation" Colloids and Surfaces A: Physicochemical and Engineering Aspects 342(1-3):136-140.*
Liu et al (2011) "Study of the interaction of DNA and histones by spin-stretching and droplet evaporation" Chinese Science Bulletin 56(12):1234-1240.*
International Search Report and Written Opinion issued in PCT/US2013/023450, dated Jun. 12, 2013.
Cerf et al., "Transfer-printing of single DNA molecule arrays on graphene high-resolution electron imaging and analysis," *Nano Letters*, 11(10):4232-4238 2011.
Cerf et al., "Ordered arrays of single DNA molecules by a combination of capillary assembly, molecular combing and soft-lithography," *Microelectronic Engineering*, 86(4-6):1419-1423 (2009).
Christina Flors, "DNA and chromatin imaging with super-resolution fluorescence microscopy based on single-molecule localization," *Biopolymers*, 95(5):290-297 (2010).
Zlatanova et al., "Stretching and imaging single DNA molecule and chromatin," *Journal of Muscle Research and Cell Motility*, 23(5-6):377-395 (2002).
Cerf et al., "Ordered arrays of native chromatin molecules for high-resolution imaging and analysis," *ACSNANO*, 6(9):7928-7934 (2012).

* cited by examiner

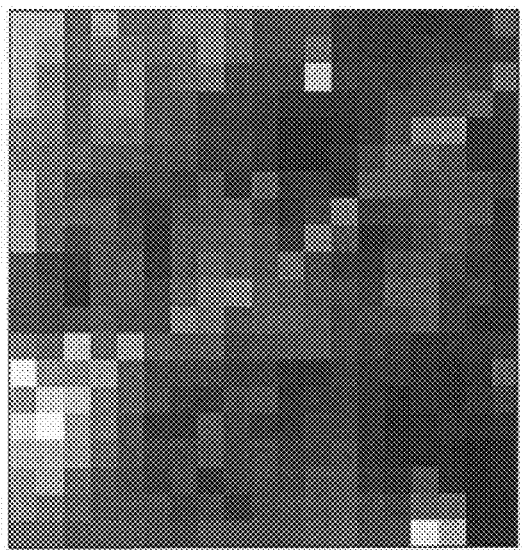
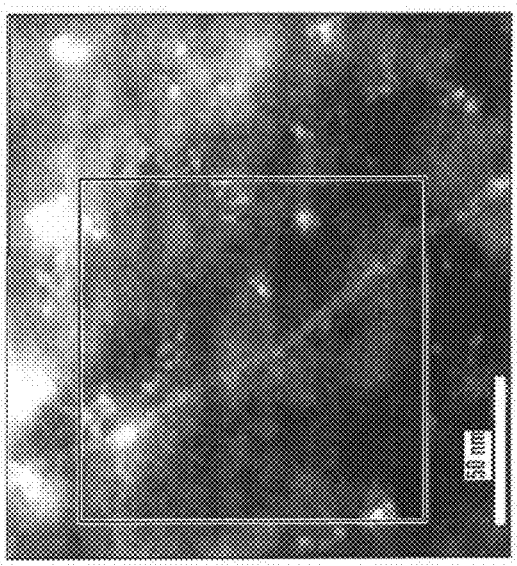
FIG. 7B
FIG. 7A

METHODS AND ARRAYS FOR CONTROLLED MANIPULATION OF DNA AND CHROMATIN FRAGMENTS FOR GENETIC AND EPIGENETIC ANALYSIS

CROSS-REFERENCE TO RELATED APPLICATIONS

This application is a U.S. National Phase filing under 35 U.S.C. §371 of International Application No. PCT/US2013/023450, filed Jan. 28, 2013, and published as WO 2013/112999-A1 on Aug. 1, 2013, which claims benefit of priority from U.S. Provisional Patent Application Ser. No. 61/591,606, filed Jan. 27, 2012, and U.S. Provisional Patent Application Ser. No. 61/667,491, filed Jul. 3, 2012. The entire contents of each of the prior applications are incorporated herein by reference in their entirety.

GOVERNMENT RIGHTS STATEMENT

This invention was made with Government support under grant number DA025722 awarded by the National Institutes of Health. The Government has certain rights in the invention.

FIELD OF THE INVENTION

The present invention relates to, inter alia, methods and arrays for use in high resolution imaging of individual nucleic acid molecules and chromatin fragments, including native chromatin fragments.

BACKGROUND OF THE INVENTION

Genetic and epigenetic information is important in understanding a number of diseases important to humans, including diseases such as Alzheimer's disease, schizophrenia, diabetes, atherosclerosis, Parkinson's disease, and cancer. Tools that enhance the ability to understand the complex genetic and epigenetic machinery relating to various diseases and conditions are crucial in developing treatments for these diseases.

Epigenetics is the study of modifications in gene expression caused by chemical modification of the chromosome with no changes in the underlying DNA sequence. Among the numerous chemical modifications, methylation of DNA at 5-cytosine is one of the most widely studied mechanisms influencing gene regulation. One of the effects of DNA methylation is to physically impede the binding of transcription factors to their recognition sites, and another is to bind methyl-CpG-binding domain (MBD) proteins involved in the modification of chromatin. In recent years, the field of epigenetics has become one of the most rapidly growing branches of molecular biology with increasing effort devoted to efficiently characterizing the human epigenome. The number of diseases suspected of being influenced by DNA methylation is growing and includes Alzheimer's disease, schizophrenia, diabetes, atherosclerosis, Parkinson's disease, cancer, among others (Schumacher et al., 2006, 310, 81-115). Interrogation of DNA methylation patterns in regulatory regions such as CpG islands has become an important tool for medical diagnostics and understanding of gene regulation. DNA methylation detection could serve, in particular, as a tool in cancer diagnosis and monitoring of treatment.

Current methods for methylation assessment and analysis include sequencing after bisulfate conversion (Cokus et al., *Nature* 2008, 452, 215), methylation-specific polymerase chain reaction (PCR) (Fraga et al., *Biotechniques* 2002, 33, 632), methylation-sensitive single-nucleotide primer extension (Ms-SNuPE) (Gonzalgo et al., *Nat. Protoc.* 2007, 2, 1931), combined bisulfate restriction analysis (COBRA) (Xiong et al., *Nucleic Acids Res.* 1997, 25, 2532), methylated DNA immunoprecipitation (Weber et al., *Nat. Genet.* 2005, 37, 853), restriction landmark genome scanning (Ando et al., *Nat. Protoc.* 2006, 1, 2774), hybridization arrays (Bibikova et al., *Genome Res.* 2006, 16, 383; Nautiyal et al., *Proc. Natl. Acad. Sci. U.S.A.* 2010, 107, 12587), among others. Efficient individual molecule analysis could reveal information lost in current ensemble methods of bulk material analysis and allow investigation of single cells. While the benefits of single molecule analyses are known and research is underway on new such methods, they are not yet available for general use. Current single molecule methods being studied include fluorescent detection of methylation in nanofluidic systems (Cipriany et al., *Anal. Chem.* 2010, 82, 2480-2487; Lim et al., *Biomicrofluidics* 2011, 5, 034106) and observation of rate dependence of polymerase activity as influenced by methylation (Flusberg et al., *Nat. Meth.* 2010, 7, 461-465). However, none of these methods is yet in general use in epigenetic analyses and the need for robust methods still exists.

Chromatin consists of repeating nucleosome units that contain two pairs of four types of histone proteins (H2A, H2B, H3 and H4) forming an octamer or eight-unit histone core, that is wrapped 1.65 turns by a 147-base length of DNA controlling access to the underlying sequence. The composition, modification and structure of chromatin plays a crucial role in gene expression. In mammalian organisms, epigenetic gene regulation functions through methylation of CpG dinucleotides and remodeling of chromatin structure through post-translational histone modifications such as acetylation, methylation, ubiquitylation, poly(ADP)ribosylation, and phosphorylation that can affect the biophysical properties and signaling of regulatory factors within the chromatin template. In the study of a variety of diseases, there is an active effort to map genome-wide genetic and epigenetic patterns across cell types, the latter in response to various environmental influences for the understanding of gene regulation and for medical diagnostics (Barski et al., *Cell.* 2007, 129, 823-837; Bernstein et al., *Cell.* 2007, 128, 669-681; Bianchi-Frias et al., *PLoS Biology.* 2004, 2, 975-990). Interrogation of chromatin modifications could serve as a tool for diagnosis and monitoring the effectiveness of treatment. In non-mammalian organisms such as drosophila, chromatin profiling would provide a means of identifying transcriptional target genes and a global view of cofactor recruitment during development (Buck et al., *Genomics.* 2004, 83, 349-360).

High resolution imaging methods, facilitated by stretching and immobilization of chromatin, may provide a direct approach to identifying epigenetic modifications throughout the genome. While the majority of current studies investigate large cell populations through coupling chromatin immunoprecipitation protocols (ChIP) with either hybridization arrays or sequencing (Heng et al., *PNAS.* 1992, 89, 9509-9513) or through Fluorescence In-Situ Hybridization (FISH)-like visualization at the gross levels of chromosomal superstructure (Smith et al., *Science.* 1992, 258, 1122-1126), few studies are aimed towards studying chromatin at the fine scale. The concept of stretching nucleic acids for analysis has been largely exploited for the study of bare DNA. Current techniques for DNA stretching comprise end-tethering, usually in combination with optical or magnetic tweezers (Smith et al., *Science*. 1996, 271, 795-799; Cerf et al., *Anal. Chem.* 2011, 83, 8073-8077), stretching on polydimethylsiloxane (PDMS) stamps (Gad et al., *J. Biomol. Struct. Dyn.* 2003, 2, 387-393; Björk et al., *Small*, 2006, 8-9, 1068-1074; Nakao et al., *Nano Lett.* 2003, 3, 1391-1394; Nakao et al., *JACS*, 2003, 125, 7162-7163; Guan et al., *PNAS*, 2005, 102, 18321-18325; Bensimon et al., *Science*. 1994, 265, 2096-2098), adsorption onto a modified surface under flow (Greene et al., *Methods Enzymol.* 2010, 472, 293-315; Perkins et al., *Science*. 1995, 268, 83-87; Tegenfeldt et al., *Phys. Rev. Lett.* 2001, 86, 1378-1381), shear flow (Smith et al., *Science*. 1999, 283, 1724-1727; Wang et al., "Microfluidic Extraction and Stretching of Chromosomal DNA from Single Cell Nuclei for DNA Fluorescence In Situ Hybridization," *Biomed. Microdevices*. 2012, in press; Tegenfeldt et al., *PNAS*. 2004, 101, 10979-10983), and nanoconfinement (Reccius et al., *Biophys. J.* 2008, 95, 273-286; Cui et al., *PNAS*. 2000, 97, 127-132). While these techniques should be transposable to chromatin, it is noticeable that chromatin stretching is less studied, except for end-tethered stretching (Bennink et al., *Nat. Struct. Biol.* 2001, 8, 606-610; Leuba et al., *PNAS*. 2003, 100, 495-500; Brower-Toland et al., *PNAS*. 2002, 99, 1960-1965; Gorman et al., *Nat. Struct. Mol. Biol.* 2010, 17, 932-938; Bancaud et al., *Nat. Struct. Mol. Biol.* 2006, 13, 444-450; Streng et al., *Lab on a Chip*. 2009, 9, 2772-2774) and a few recent nanoconfinement studies (Cipriany et al., *Anal. Chem.* 2010, 82, 2480-2487; Ersfeld, K., *Meth. in Mol. Biol.* 2004, 270, 395-402). The most popular stretching technique for FISH-like genetic or epigenetic analysis relies on cell shearing after fixation, the latter leading to poor molecule to molecule repeatability (Smith et al., *Science*. 1992, 258, 1122-1126; Sims et al., *J. Biol. Chem.* 2006, 281, 12760-12766). As an example, chromatin fibers from *drosophila* and human cells have been spread by direct lysis onto charged microscope slides to show the organization of covalently modified histones in silent chromatin sequences (Blower et al., *Dev. Cell.* 2002, 2, 319-330), DNA replication timing in centromeric regions (Lam et al., *PNAS*. 2006, 103, 4186-4191; Sullivan et al., *Nat. Struct. Mol. Biol.* 2004, 11, 1076-1083; Cohen et al., *Epigenetics & Chromatin*. 2009, 2, 6), and to study distribution of GINS complex (Daban, J. R., *Micron*. 2011, 42, 733-750). Other studies involve stretching chromatin fibers to establish a mapping between spatial location and genomic location (Smith et al., *Science*. 1992, 258, 1122-1126; Greene et al., *Methods Enzymol.* 2010, 472, 293-315) or for morphological studies using transmission electron microscopy and atomic force microscopy (Lyubchenko et al., *Methods*. 2009, 47, 206-213). In recent years, progress has been made in employing new technologies with the potential to bridge the gap between static structural features and dynamic physiological processes in the study of biomolecules, while increasing spatial resolution (Kobayashi et al., *Ultramicroscopy*. 2007, 107, 184-190; Ando et al., *Pflugers Arch.* 2008, 456, 211-225; Cerf et al., *J. Mater. Res.* 2010, 26, 336-346). Yet, to our knowledge, no method has been demonstrated that allows the controllable stretching and isolation of canonical and native chromatin molecules for high-throughput analyses while being compatible with high-resolution imaging techniques.

The present invention is directed to overcoming these and other deficiencies in the art.

SUMMARY OF THE INVENTION

In one aspect, the present invention relates to a chromatin array for use in high resolution imaging of native chromatin fragments. The chromatin array includes a transfer platform having a support and a transfer surface layered on the support. The chromatin array also includes a plurality of elongated individual native chromatin fragments coupled to the transfer surface in an orderly pattern suitable for high resolution imaging of the plurality of native chromatin fragments. The native chromatin fragments of the chromatin array include both DNA and histones.

In another aspect, the present invention relates to a method of producing a chromatin array for use in high resolution imaging of native chromatin fragments, where this method includes: (a) providing a plurality of elongated individual native chromatin fragments removably coupled to a hydrophobic component in an orderly pattern suitable for high resolution imaging of the plurality of native chromatin fragments, where the native chromatin fragments include both DNA and histones; and (b) transferring the plurality of elongated individual native chromatin fragments to a transfer platform, thereby yielding a chromatin array including the plurality of elongated individual chromatin fragments attached to the transfer platform in said orderly pattern. The transfer platform of this method includes a support and a transfer surface layered on the support; and is effective to receive and capture the plurality of elongated individual chromatin fragments in the orderly pattern from the hydrophobic component. In one embodiment, this method further includes labeling the native chromatin fragments with at least one label for imaging or assaying purposes. The present invention also includes a chromatin array produced according to this method.

In another aspect, the present invention relates to a method of high resolution imaging and analysis of native chromatin, where this method includes: (a) providing a plurality of native chromatin fragments; (b) immobilizing the plurality of native chromatin fragments to a transfer platform in an orderly pattern suitable for high resolution imaging of the plurality of native chromatin fragments, where the native chromatin fragments include both DNA and histones; and (c) conducting high resolution imaging and analysis of the native chromatin fragments.

In another aspect, the present invention relates to a method of producing a chromatin array for use in high resolution imaging of native chromatin fragments, where this method includes: (a) providing a plurality of suspended individual native chromatin fragments; (b) providing a hydrophobic component that includes a micro/nanostructured capture array having a hydrophobic surface that has topographical features effective to assist in capillary-based trapping and elongation of individual native chromatin fragments in an orderly pattern; and (c) elongating the plurality of individual native chromatin fragments on the micro/nanostructured capture array so as to immobilize the individual native chromatin fragments in an orderly pattern to the hydrophobic surface of the micro/nanostructured capture array. The native chromatin fragments of this method include both DNA and histones. In one embodiment, this method further includes labeling the native chromatin fragments with at least one label for imaging or assaying purposes. The present invention also relates to a chromatin array produced according to this method.

In another aspect, the present invention relates to a method of producing a nucleic acid molecule imaging array for use in high resolution imaging of individual nucleic acid molecules, where this method includes: (a) providing at least one individual elongated nucleic acid molecule removably coupled to a hydrophobic component; and (b) transferring the at least one individual elongated nucleic acid molecule to a transfer platform in the absence of solvent mediation, thereby yielding a nucleic acid molecule imaging array effective for use in high resolution imaging of the at least one elongated individual nucleic acid molecule. The transfer platform of this method includes a support having a hydrophilic surface. The transfer platform is also effective to receive and capture, in the absence of solvent mediation, the at least one elongated individual nucleic acid molecule from the hydrophobic component. The present invention also relates to a nucleic acid molecule imaging array produced according to this method.

In another aspect, the present invention relates to a method of high resolution imaging and analysis of a plurality of individual nucleic acid molecules, where the method includes: (a) providing a nucleic acid molecule imaging array produced according to the method of the present invention for making such nucleic acid imaging arrays; and (b) conducting high resolution imaging and analysis of the individual elongated nucleic acid molecules on the nucleic acid molecule imaging array.

Generally, in various aspects, the present invention described herein relies on being a straightforward, low-cost and high-throughput method to controllably isolate and manipulate single chromatin fragments onto various solid supports for high-resolution imaging and analysis of multiple genetic and epigenetic marks within individual fragments.

The present invention relates to, inter alia, the controlled isolation and manipulation of individual chromatin fragments to form ordered arrays molecules onto various supports for subsequent imaging and parallel analysis of these fragments. In various embodiments, the analysis is performed using fluorescence microscopy, atomic force microscopy, scanning tunneling microscopy, near field optical microscopy or electron microscopy, with electron microscopy providing the possibility to resolve the genomic location of epigenetic marks with single base resolution.

The present invention is effective for use with various types of cells, including without limitation, mammalian and cancer cell lines in their native state. Further, the present invention is useful for high-throughput and large screening applications. In one aspect, the present invention relates to methods and devices that provide a molecular beads-on-a-string configuration that is compatible for use with high-resolution imaging and analyses using atomic force microscopy (AFM). The methods and devices of the present invention are effective for the preservation of histones during the processing steps of the present invention.

In one embodiment of the process of the present invention, the chromatin molecules are first functionalized in bulk with genetic or epigenetic probes of interest either fluorescently-labeled or compatible with high-resolution microscopy. A controlled volume of labelled-chromatin fragments in solution is injected between a fixed glass spreader and a topographically microstructured polydimethylsiloxane stamp. The liquid contact line is moved over the stamp at a controlled and finely tuned velocity. Chromatin fragments are partially trapped inside the microfeatures of the stamp and elongated while preserving their native and intrinsic structure. The so-assembled chromatin fragments can then be transfer-printed with high placement accuracy and yield onto a hydrophilic or a hydrophobic substrate such as glass cover slips for optical or scanning-probe imaging (conventional fluorescence microscopy, super-resolution microscopy, atomic force microscopy, or near field optical microscopy), but also single-layer graphene support layers on TEM grids for electron imaging and morphological/elemental composition studies.

This methodology enables for the first time the controlled manipulation of native chromatin fragments and the simultaneous and high-resolution mapping of multiple epigenetic marks within individual chromatin fragments.

In one embodiment, to make and use the invention, a microstructured PDMS stamp is placed on a translation stage with fine speed regulation. Chromatin fragments and labels of interest are mixed in solution. A 15 ul droplet of labeled chromatin fragments in solution is squeezed between the PDMS and a fixed glass spreader. As the liquid meniscus is dragged over the PDMS stamp's surface at controlled speed, the meniscus encounters the topographical wells of the PDMS stamp and gets pinned during a given time. During this pinning time, the molecules are trapped inside the wells by the capillary forces exerted and stretched when the meniscus finally disrupts. If the displacement speed and the concentration of the chromatin molecules in solution are properly tuned, single molecules can be trapped and simultaneously stretched inside each topographical well of the PDMS stamp, leading to an array of single chromatin molecules at the surface of the PDMS stamp.

FIGS. 1-19 illustrate various aspects of the present invention.

With regard to the capillary assembly mechanism (see FIGS. 1, 9, and 11), the following is a description thereof: (A) The meniscus is dragged over the PDMS stamp; (B) during the meniscus' pinning time, the molecules are trapped inside the PDMS cavities; (C) the elastic energy stored exceeds the pinning energy and the meniscus disrupts releasing and simultaneously stretching the trapped chromatin molecules; and (D) the chromatin molecules are assembled into regular arrays on the PDMS stamp.

In one embodiment of the present invention, the resulting chromatin array can then be transferred onto any analysis support (glass cover slips, TEM grids, mica sheets, silicon wafers) compatible with the characterization tool to be used for further imaging and analysis.

In other embodiments, the invention is compatible with any type of analysis support. The resulting chromatin array can be transferred onto glass cover slips, TEM grids, mica sheets, silicon wafers, etc . . . to be imaged and analyzed using different characterization tools (fluorescence microscopy, scanning-probe microscopy, electron microscopy). This invention can be used for chromatin but also higher-ordered structures.

As noted herein, the present invention can be used for various applications. One particular application includes, but is not limited to, high-resolution imaging and analysis of individual chromatin fragments for genetic and epigenetic studies. This would enable a better understanding of gene regulation and disease.

The present invention also improves on aspects relating to systems, methods, and arrays described herein. As noted, conventionally, in biology, DNA is studied and characterized in its compacted state hindering valuable information. The organic composition of DNA renders it difficult to image using electron microscopy techniques that limits the use of electron beams for analysis of biological molecules. Graphene is a remarkable material that has received great interest over the past decade as it enables high contrast imaging when used as support for Scanning Electron Microscopy (SEM) or Transmission Electron Microscopy (TEM). In one embodiment, the present invention provides for the assembly of single stretched DNA molecules or chromatin fragments into regular arrays deposited on a microstructured PDMS (Polydimethylsiloxane) stamp by means of capillary assembly, and transferring this assembly from the PDMS stamp to a graphene surface (e.g., graphene TEM grids) using solvent mediation. As a result, the invention allows obtaining individual elongated molecules at predetermined locations on a graphene surface, which then enables high throughput electron beam imaging and analysis with single nucleotide resolution.

Currently, TEM imaging of DNA is generally conducted by incubating coiled DNA at the surface of a TEM grid and staining it for imagery contrast. On the contrary, the present invention provides a straightforward, low-cost and high-throughput system and method to elongate and transfer single DNA molecules (chromatin fragments, DNA-protein complexes) on graphene surfaces in one-step. This invention enables imaging of DNA with single nucleotide resolution using Electron Microscopy.

Referring now to FIG. 1, in one non-limiting embodiment of this invention, a microstructured PDMS stamp is placed on a translation stage with speed regulation. A droplet (e.g., about 10-40 μl) of DNA in solution is squeezed between the PDMS and a fixed glass spreader. As the liquid meniscus is dragged over the PDMS stamp's surface at controlled speed, the meniscus encounters the topographical wells of the PDMS stamp and gets pinned during a given time. During this pinning time, the molecules are trapped inside the wells by the capillary forces exerted and stretched when the meniscus finally disrupts. If the displacement speed and the concentration of the DNA molecules in solution are properly tuned, (as an example, about 0.5-1 mm/sec and about 1-10 μg/mL, respectively), single molecules can be trapped and simultaneously stretched inside each topographical well of the PDMS stamp, leading to an array of single DNA molecules at the surface of the PDMS stamp. The dimensions of the PDMS wells can be nanometric or micrometric, comprised between about 100 nm and about 100 μm in diameter, these dimensions being only limited by the lithography technique used to fabricate them. If we consider the example of phage lambda DNA molecules in particular, the PDMS features used to elongate and order the molecules measure about 3-8 μm in diameter and about 3-5 μm deep, with about 20-30 μm spacing between them.

Referring now to FIG. 2, in another non-limiting embodiment of the invention, the obtained DNA assembly can then be transferred on a graphene TEM grid. First, the TEM grid is scotch-taped on a surface and a droplet of absolute ethanol is deposited on top. Ethanol is left to evaporate but not completely. The PDMS stamp with assembled DNA molecules is then brought into contact with the wet graphene TEM grid for 2 minutes. Finally, the PDMS stamp is peeled off, leaving the DNA assembly at the surface of the graphene TEM grid.

This process is extremely clean and free of any contamination. No further labeling of the molecules or staining of the grid is required.

The transfer protocol as shown in FIG. 2 can be extended to any type of hydrophobic surfaces. Solvents other than ethanol can be used to mediate the transfer process. This invention can be used for DNA but also other kinds of biological entities or inorganic components.

The present invention may be used for high-resolution imaging and analysis of DNA for genetic or epigenetic studies. Furthermore, this invention could be applied to transferring more complex assemblies and generally expand the uses of electron microscopy in the field of biomolecular analysis.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

The patent or application file contains at least one drawing executed in color. Copies of this patent or patent application publication with color drawings will be provided by the U.S. Patent and Trademark Office upon request and payment of the necessary fee.

FIG. 4B corresponds to a zoomed image of FIG. 4A.

In FIG. 5A, the dashed circle outlines a piece of exfoliated graphene. One can also observe the imprints of the PDMS stamp's microfeatures. In FIG. 5B, the dashed area corresponds to the same piece of graphene outlined in FIG. 5A. One can observe the array of the nucleic acid stained DNA molecule array (488 nm excitation). In FIG. 5C, the scanned area corresponds to the same area outlined in FIG. 5A and FIG. 5B, where one can recognize the exfoliated graphene piece on the bottom right surrounded by silicon dioxide. FIG. 5D shows magnified atomic force microscope images and the corresponding cross-sections of the delimited areas in Figure C. FIG. 5D (top row) shows a single DNA molecule on silicon dioxide, FIG. 5D (bottom row) shows a single DNA molecule on exfoliated graphene.

FIG. 6A: Fluorescence image of a lacey carbon TEM grid with suspended single layer graphene after transfer of the nucleic acid stained DNA array. The arrows indicate the bright spots that are part of the periodic DNA molecule array. The DNA strands are not visible due to quenching effects. FIG. 6B: Transmission electron micrograph of elongated phage lambda DNA molecules on single layer graphene. The DNA molecules are not nucleic acid stained in this case. The distance between the molecules is short probably because the view shows adjacent patterns where one molecule is stretched up to the next pattern, nearly meeting the next molecule. FIG. 6C and FIG. 6D are higher magnification micrographs of the molecule on the right in FIG. 6B. The inset in FIG. 6D shows a theoretical computer-simulated representation of B-form DNA. It is observed that the pitch measured from the TEM micrograph is 1.35 times greater than the theoretical pitch of a B double helix.

FIGS. 7A-7C show the results of an EELS analysis. On the left (FIG. 7A), bright field image of a single DNA molecule. The frame corresponds to the scanned area for EELS. In the center (FIG. 7B), 20×20 EELS map from the insert in 7A, after energy filtering at 130 eV ($PL_{23}$ edge of phosphorous). This map was acquired with a 4 s dwell time per pixel. On the right (FIG. 7C), accumulation of EELS spectra extracted from the 20×20 map without energy filtering (90 eV-1140 eV window). The insert corresponds to the sum of pixels along the molecule only, with a background substraction (the energy window is reduced to 120 eV-200 eV). One can recognize the $L_{23}$ edge of phosphorous.

(FIG. 12B) corresponds to a 1.5× zoom of image (FIG. 12A).

(FIG. 13A) represents a large scan view where we notice the positioning of two chromatin molecules as indicated by the red arrows. (FIG. 13B) represents an enlargement of the area outlined in (FIG. 13A). The insert corresponds to the cross-section measurements performed across the chromatin segment. (FIG. 13C) depicts a 3D representation of the chromatin molecule shown in (FIG. 13B). (FIG. 13D) is a high-resolution image of the chromatin molecule showing nucleosome distribution and positioning along one section of the stretched chromatin molecule.

(FIG. 14A). Fluorescence micrograph taken at 475 nm excitation. (FIG. 14B). Fluorescence micrograph from the same area taken at 620 nm. Histones H3 (shown in false red FIG. 14B) are colocalized with DNA (shown in false green FIG. 14A).

FIG. 18A: Fluorescence micrograph taken at 475 nm excitation. FIG. 18B: Fluorescence micrograph from the same area taken at 620 nm. FIG. 18C: Overlay image from FIG. 18A and FIG. 18B. Histones H3 (shown in false red) are colocalized with DNA (shown in false green).

FIG. 19A represents a large scan view where we notice the positioning of four chromatin molecules as indicated by the white arrows. FIG. 19B represents an enlargement of a chromatin molecule that is part of the array, showing nucleosome distribution and positioning along the stretched chromatin molecule.

DETAILED DESCRIPTION OF THE INVENTION

Figure 1:
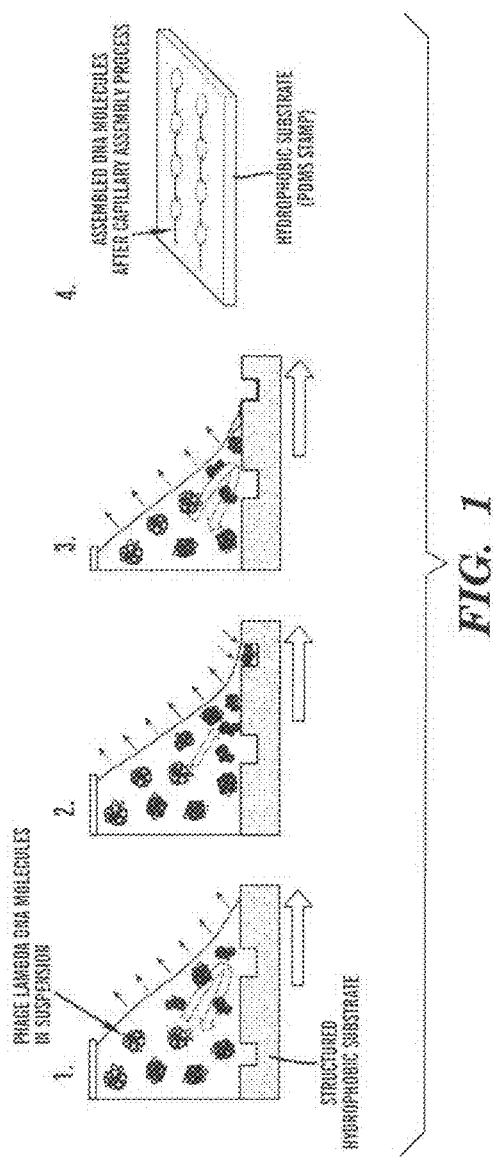
FIG. 1 is a schematic representation of one embodiment of a capillary assembly procedure of the present invention. Step 1: The liquid meniscus is dragged over the microstructured PDMS stamp. Step 2: The meniscus encounters the topographical features, gets pinned during a given time, and during this pinning time the molecules are trapped inside the wells by the capillary forces exerted. Step 3: The meniscus finally disrupts and releases the molecules while stretching them. Step 4: Final assembly of individual DNA molecule arrays on the microstructured PDMS stamp.

The present invention relates to, inter alia, methods and arrays for use in high resolution imaging of individual nucleic acid molecules and chromatin fragments, including native chromatin fragments. Thus, the present invention may be used for high-resolution imaging and analysis of nucleic acid molecules and chromatin for genetic or epigenetic studies, and generally expands the uses of various high resolution imaging techniques in the field of biomolecular analysis. The chromatin and nucleic acid molecules used in the arrays and methods of the present invention can be from any source. For example, the source of chromatin fragments or nucleic acid molecules can be a mammal or a non-mammal, and more specifically can be an animal, a plant, a fungus, a bacterium, an algae, a protozoan, a virus, etc. Further, as discussed herein, the present invention is effective in providing a plurality of individual native chromatin fragments and/or nucleic acid molecules that are of various lengths. For example, in one embodiment, the individual native chromatin fragments or nucleic acid molecules can be of a length of between about 5-100 kbp and extended to their contour lengths.

The present invention provides a chromatin array for use in high resolution imaging of native chromatin fragments. The chromatin array includes a transfer platform having a support and a transfer surface layered on the support. The chromatin array also includes a plurality of elongated individual native chromatin fragments coupled to the transfer surface in an orderly pattern suitable for high resolution imaging of the plurality of native chromatin fragments. The native chromatin fragments of the chromatin array include both DNA and histones. In one embodiment, the native chromatin fragments are coupled to the transfer surface in a beads-on-a-string conformation. In another embodiment, the native chromatin fragments are labeled. In a particular embodiment, the chromatin DNA is labeled. In another particular embodiment, the chromatin histones are labeled.

The transfer surface can include any layer effective to immobilize at least a portion of the individual native chromatin fragments to the support of the transfer platform. In certain embodiments, the transfer surface can be the surface of the support. The transfer surface can be hydrophobic, hydrophilic, include portions that are hydrophobic and portions that are hydrophilic, or functionalized to have a hydrophilic surface. In embodiments that include a transfer platform that has a hydrophobic transfer surface, solvent mediation may be used to transfer the native chromatin fragments thereto. Solvent mediation is further described herein.

Suitable hydrophobic transfer surfaces for use in this invention can include, without limitation, graphene, a graphene blend, a graphene derivative, a graphene-like compound, a thermoplastic, polycarbonate, vinyl, a silanized surface, an elastomer such as polydimethylsiloxane, a metal, a plastic, molybdenum, silicon, silicon nitride, copper, gold, carbon, and the like.

As discussed herein, the transfer surface can also be hydrophilic or functionalized to have a hydrophilic surface. Therefore, in certain embodiments, the transfer surface can be hydrophobic and then functionalized to have a hydrophilic surface. In such an embodiment, solvent mediation can be avoided.

Suitable hydrophilic transfer surfaces or transfer surfaces functionalized to have a hydrophilic surface can include materials such as, but not limited to, silicon, silicon dioxide ($SiO_2$), glass, mica, a surface functionalized with hydrophilic functional groups, quartz, a silanized surface, a surface functionalized with hydroxyl groups, and the like.

As used herein, the term "high resolution imaging" refers imaging techniques or other assaying techniques that include, without limitation, optical imaging, optical tweezers technology, fluorescence microscopy, scanning probe microscopy (e.g., atomic force microscopy), transmission electron microscopy (TEM), scanning transmission electron microscopy (STEM), electron energy loss spectroscopy (EELS), scanning electron microscopy (SEM), electron tomography, energy-filtered transmission electron microscopy (EFTEM), X-ray spectroscopy, Auger electron spectroscopy, and the like.

The present invention also provides a method of producing a chromatin array for use in high resolution imaging of native chromatin fragments, where this method includes: (a) providing a plurality of elongated individual native chromatin fragments removably coupled to a hydrophobic component in an orderly pattern suitable for high resolution imaging of the plurality of native chromatin fragments, where the native chromatin fragments include both DNA and histones; and (b) transferring the plurality of elongated individual native chromatin fragments to a transfer platform, thereby yielding a chromatin array including the plurality of elongated individual chromatin fragments attached to the transfer platform in said orderly pattern. The transfer platform of this method includes a support and a transfer surface layered on the support; and is effective to receive and capture the plurality of elongated individual chromatin fragments in the orderly pattern from the hydrophobic component. In one embodiment, this method further includes labeling the native chromatin fragments with at least one label for imaging or assaying purposes. The present invention also includes a chromatin array produced according to this method.

In one embodiment of this method, the hydrophobic component includes a micro/nanostructured capture array having a hydrophobic surface that has topographical features effective to assist in capillary-based trapping and elongation of individual native chromatin fragments in an orderly pattern.

In one embodiment, this method can further include labeling the native chromatin fragments with at least one label for imaging or assaying purposes. The native chromatin fragments can be labeled with more than one different type of label for imaging or assaying purposes. Further, the labeling can include either bulk labeling of the native chromatin fragments prior to transferring them to the transfer platform or direct labeling of the native chromatin fragments after transferring them to the transfer platform. In certain embodiments, the DNA is labeled, the histones are labeled, or both the DNA and histones are labeled.

Suitable transfer surfaces for use in this method are as described herein.

In one embodiment of this method, the plurality of elongated individual native chromatin fragments are transferred to the transfer platform using solvent mediation. As provided herein, solvent mediation is useful when the transfer surface of the transfer platform is hydrophobic.

The present invention also provides a method of high resolution imaging and analysis of native chromatin, where this method includes: (a) providing a plurality of native chromatin fragments; (b) immobilizing the plurality of native chromatin fragments to a transfer platform in an orderly pattern suitable for high resolution imaging of the plurality of native chromatin fragments, where the native chromatin fragments include both DNA and histones; and (c) conducting high resolution imaging and analysis of the native chromatin fragments.

The present invention also provides a method of producing a chromatin array for use in high resolution imaging of native chromatin fragments, where this method includes: (a) providing a plurality of suspended individual native chromatin fragments; (b) providing a hydrophobic component that includes a micro/nanostructured capture array having a hydrophobic surface that has topographical features effective to assist in capillary-based trapping and elongation of individual native chromatin fragments in an orderly pattern; and (c) elongating the plurality of individual native chromatin fragments on the micro/nanostructured capture array so as to immobilize the individual native chromatin fragments in an orderly pattern to the hydrophobic surface of the micro/nanostructured capture array. The native chromatin fragments of this method include both DNA and histones. In one embodiment, this method further includes labeling the native chromatin fragments with at least one label for imaging or assaying purposes. The present invention also relates to a chromatin array produced according to this method.

In one embodiment, this method further includes labeling the native chromatin fragments with at least one label for imaging or assaying purposes. In a particular embodiment, the native chromatin fragments are labeled with more than one different type of label for imaging or assaying purposes. In certain embodiments, the labeling can be either bulk labeling of the native chromatin fragments prior to elongating them on the micro/nanostructured capture array or direct labeling of the native chromatin fragments after transferring them to the micro/nanostructured capture array. In other embodiments, the DNA is labeled, the histones are labeled, or both the DNA and histones are labeled.

The hydrophobic surface of the micro/nanostructured capture array can be a polymer material selected from the group consisting of poly(dimethylsiloxane), parylene, poly (methylmethacrylate), polyethylenes, vinyls, and acrylates.

The present invention also provides a method of producing a nucleic acid molecule imaging array for use in high resolution imaging of individual nucleic acid molecules, where this method includes: (a) providing at least one individual elongated nucleic acid molecule removably coupled to a hydrophobic component; and (b) transferring the at least one individual elongated nucleic acid molecule to a transfer platform in the absence of solvent mediation, thereby yielding a nucleic acid molecule imaging array effective for use in high resolution imaging of the at least one elongated individual nucleic acid molecule. The transfer platform of this method includes a support having a hydrophilic surface. The transfer platform is also effective to receive and capture, in the absence of solvent mediation, the at least one elongated individual nucleic acid molecule from the hydrophobic component. The present invention also relates to a nucleic acid molecule imaging array produced according to this method.

In some embodiments, the hydrophilic surface of the support of the transfer platform can be made of a material or composition that includes, without limitation, silicon, silicon dioxide ($SiO_2$), glass, mica, a surface functionalized with hydrophilic functional groups, quartz, a silanized surface, a surface functionalized with hydroxyl groups, and the like.

As used herein with regard to this method, the term "nucleic acid molecules" refers to deoxyribonucleic acid (DNA) molecules, ribonucleic acid (RNA) molecules, and mixtures thereof. The nucleic acid molecules can be from any source, including, without limitation, from an animal (including humans), a plant, a fungus, a bacterium, an algae, a protozoan, or a virus. Further, this method is effective to elongate the nucleic acid molecules to various lengths. For example, in one embodiment, the individual nucleic acid molecules can be of a length of between about 5-100 kbp and extended to their contour lengths.

As used herein, the term "capillary-based trapping and elongation of individual native chromatin fragments" generally refers to any technique that uses capillary action to capture and then elongate a single chromatin fragment on a surface. As used herein, the term "capillary-based trapping and elongation of individual nucleic acid molecules" generally refers to any technique that uses capillary action to capture and then elongate a single nucleic acid molecule on a surface. For example, one suitable technique is commonly referred to as molecular combing, which has been described in U.S. Pat. No. 5,840,862, the disclosure of which is hereby incorporated by reference herein. U.S. Pat. No. 5,840,862 describes the idea of attaching DNA from one of its extremities to a surface and stretching the molecule by displacement of the meniscus of solvent containing the molecules, relative to the surface.

As used herein, the term "solvent mediation" refers to a method or technique that involves the use of a solvent to transfer a nucleic acid molecule from one surface to another surface. In one embodiment, the solvent used in the solvent mediation of the present invention can include, without limitation, ethanol, isopropanol, and aqueous solutions.

The hydrophobic surface of the micro/nanostructured capture array can be made of any hydrophobic material suitable for solvent mediation of the individual nucleic acid molecules from the micro/nanostructured capture array to the transfer platform. In one embodiment, the hydrophobic surface includes a polymer material. Examples of suitable polymer materials for use as the hydrophobic surface can include, without limitation, poly(dimethylsiloxane) (PDMS), parylene, poly(methylmethacrylate), polyethylenes, vinyls, and acrylates.

The hydrophobic surface of the micro/nanostructured capture array can be configured to have a variety of topographical features, as long as such features are effective to assist in capillary-based trapping and elongation of individual nucleic acid molecules. Various materials and methods of capillary-based trapping and elongation of individual nucleic acid molecules are known in the relevant art to those of ordinary skill. Thus, the present invention contemplates a micro/nanostructured capture array having a hydrophobic surface having topographical features that are known in the art for the above-identified function.

In one embodiment, the topographical features of the hydrophobic surface of the micro-nanostructured capture array can include, without limitation, one or more micro/ nanowell. As used herein, the term "micro/nanowell" refers to a well-like structure of the micro/nanostructured capture array that has a depth or diameter (e.g., opening region at the surface) that is measured in micrometers or nanometers. For example, in one embodiment, the micro/nanowells have a diameter of between about 10 nanometers (nm) and about 50 micrometers ($\mu$m), and a depth of between about 10 nm and about 50 µm. In another embodiment, the micro/nanowells can have a diameter of between about 80 nm and about 50 µm, and in a another embodiment can have a diameter of between about 100 nm and about 50 µm Without any intent to being limited thereto, in a particular embodiment, the micro/nanowells can have a diameter of between about 3 µm and about 8 µm, a depth of between about 3 µm and about 5 µm, and a spacing between them of between about 20 µm and about 30 µm.

The micro/nanowells are fabricated using conventional photolithography. In practice, the fabrication of the micro/nanostructured hydrophobic surface first involves the fabrication of a micro/nanostructured silicon master. The silicon micro/nanostructured master is fabricated using photolithography for micrometric features, and using electron beam lithography in the case of nanometric features. Once the silicon master is generated with the desired protruding features, it undergoes a silanization step where a hydrophobic silane molecule is used to coat its surface. Then, an elastomer material, such as polydimethylsiloxane (PDMS), is poured in its liquid form onto the structured silicon master and cured in an oven (e.g., at 80° C. for 2 hours). The casted elastomer material (e.g., PDMS material) is finally peeled away, resulting in a PDMS replication of the initial silicon master's features. This PDMS replication thus consists of micro/nanowells that are then used as topographical pinpoints during the molecular elongation process.

In a particular embodiment, the hydrophobic surface is a plurality of micro/nanowells. The plurality of micro/nanowells can be of various arrangements. For example, the micro/nanowells can have substantially the same three-dimensional size and shape, or they can have a different three-dimensional sizes and a different three-dimensional shapes. The plurality of micro/nanowells can also be arranged in an orderly pattern (e.g., like rows and columns of a grid), or a more random pattern.

Examples of suitable shapes of the micro/nanowells can include, without limitation, asymmetric shapes, elliptical shapes, crosses, slots, drop-like shapes, triangular, square, rectangular, circular, and the like. In some embodiments, the micro/nanowells can have a diameter of between about 10 nanometers (nm) and about 50 micrometers (µm), although the present invention is not limited to any particular diameter dimensions. In some embodiments, the micro/nanowells have a diameter of between about 3 µm and about 8 µm, a depth of between about 3 µm and about 5 µm, and a spacing between them of between about 20 µm and about 30 µm, although the present invention is not limited to any particular combination of diameter, depth, or spacing dimensions.

With regard to the transfer platform, the hydrophobic substrate of the transfer platform can be made of a graphene-containing hydrophobic compound including, without limitation, graphene, a graphene blend, a graphene derivative, a graphene composite, and/or a graphene-like compound, as long as such compounds are hydrophobic. In one embodiment, the hydrophobic substrate is layered onto the support of the transfer platform at a thickness to allow electrons to pass through the hydrophobic substrate. In a more particular embodiment, the thickness of the hydrophobic substrate is less than about 50 nanometers.

In one embodiment, the hydrophobic substrate is deposited onto the transfer platform by means of a transfer protocol in liquid or gas phase. For example, the hydrophobic substrate can be configured on a bottom substrate, which is ordinarily, but not always, made of a metal. A suitable transfer protocol includes the prior deposition of a top additive/intermediate material onto the hydrophobic substrate to preserve its mechanical integrity during the transfer protocol. The hydrophobic material is released from all underlying substrates by etching in the liquid phase. The support of the transfer platform is used from the liquid phase to scoop the hydrophobic material onto it, out of the liquid phase. The transfer platform thus constituted is dried to allow proper deposition and adsorption to the surfaces of the support. The top of the transfer protocol additive/intermediate material is dissolved at the end of the transfer protocol to allow the deposition and adsorption of the hydrophobic material onto the patterns of the transfer platform.

The support of the transfer platform can be made of materials such as silicon dioxide ($SiO_2$), molybdenum, silicon, silicon nitride, copper, gold, and carbon. The support can be prepared by manufacturing a network of through-hole apertures using conventional lithography techniques. A typical transfer platform of this kind is commercially available from manufacturers such as Ted Pella, Pacific Grid Tech, 2 spi, Gilder Grids, and Agar Scientific, etc.

The hydrophobic component for use in this method can include a micro/nanostructured capture array having a hydrophobic surface having topographical features effective to assist in capillary-based trapping and elongation of individual nucleic acid molecules. Suitable micro/nanostructured capture arrays are as described herein.

Suitable transfer platforms for use in this method are as described herein above, and particularly include hydrophobic substrates made of graphene, a graphene blend, a graphene derivative, a graphene composite, or a graphene-like compound.

Referring now to FIG. 1, in one non-limiting embodiment of this invention, a microstructured PDMS stamp is placed on a translation stage with speed regulation. A droplet (e.g., about 10-40 µl) of DNA in solution is squeezed between the PDMS stamp and a fixed glass spreader. As the liquid meniscus is dragged over the PDMS stamp's surface at a controlled speed, the meniscus encounters the topographical wells of the PDMS stamp and gets pinned during a given time. During this pinning time, the molecules are trapped inside the wells by the capillary forces exerted and stretched when the meniscus finally disrupts. If the displacement speed and the concentration of the DNA molecules in solution are properly tuned—as an example, about 0.5-1 mm/sec and about 1-10 µg/mL, respectively—single molecules can be trapped and simultaneously stretched inside each topographical well of the PDMS stamp, leading to an array of single DNA molecules at the surface of the PDMS stamp. In certain embodiments, with respect to displacement speed for use in trapping elongated chromatin fragments, the speed can be adjusted to lower speeds including, without limitation, to speeds of between about 0.01-0.02 mm/sec.

The dimensions of the PDMS wells can be nanometric or micrometric as noted herein above. In one embodiment, the PDMS wells are between about 10 nm and about 100 µm in diameter, and more particularly between about 100 nm and about 50 µm in diameter. The depth of such wells is as described herein above for micro/nanowells. As understood by those of ordinary skill in the art, these dimensions are only limited by the lithography technique used to fabricate them. In the context of the phage lambda DNA molecules in particular, the PDMS features used to elongate and order the molecules measure about 3-8 µm in diameter and about 3-5 µm deep, with about 20-30 µm spacing between them. One of ordinary skill in the art can determine other particular parameters of the PDMS wells (micro/nanowells), depending on the type of DNA molecules they are interested in studying.

Figure 2:
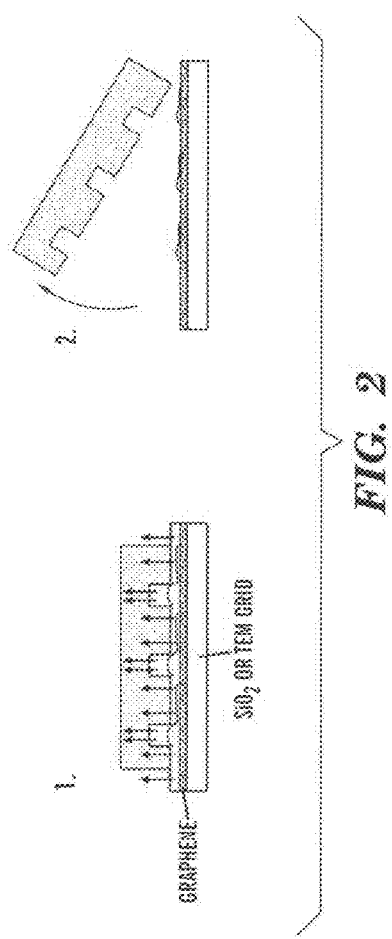
FIG. 2 is a schematic representation of one embodiment of a transfer-printing with solvent mediation procedure of the present invention. Step 1: A droplet of solvent (e.g., ethanol) is deposited on a substrate (e.g., a graphene substrate) and the PDMS stamp with assembled DNA molecules is put in contact with the wet surface. Step 2: The PDMS stamp is removed from the surface leaving the DNA molecules at the surface of the substrate (e.g., the graphene substrate).
Figure 3:
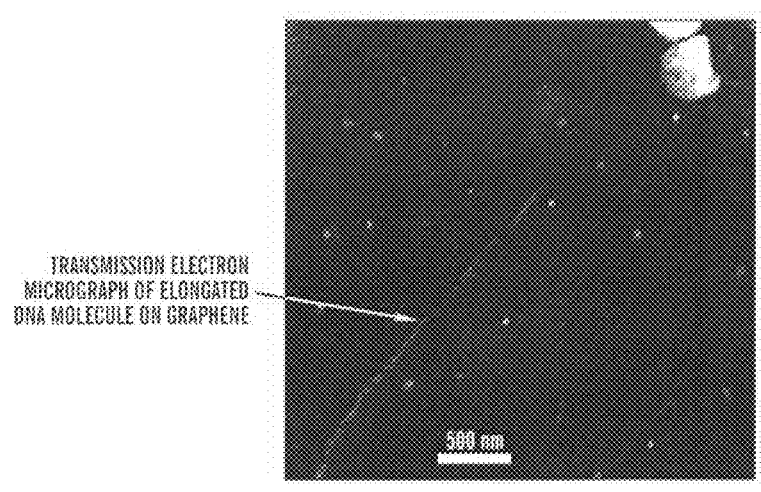
FIG. 3 is a transmission electron micrograph of elongated DNA molecule on a graphene substrate.

Referring now to FIG. 2, in another non-limiting embodiment of the present invention, the obtained DNA assembly can then be transferred onto a graphene TEM grid. First, the TEM grid is scotch-taped on a surface and a droplet of absolute ethanol is deposited on top. Ethanol is left to evaporate, but not completely. The PDMS stamp with assembled DNA molecules is then brought into contact with the wet graphene TEM grid for 2 minutes. Finally, the PDMS stamp is peeled off, leaving the DNA assembly at the surface of the graphene TEM grid. This process is extremely clean and free of any contamination. No further labeling of the molecules or staining of the grid is required.

The transfer protocol as shown in FIG. 2 can be extended to any type of hydrophobic surfaces. Solvents other than ethanol can be used to mediate the transfer process.

The present invention also provides a method of high resolution imaging and analysis of a plurality of individual nucleic acid molecules, where the method includes: (a) providing a nucleic acid molecule imaging array produced according to the method of the present invention for making such nucleic acid imaging arrays; and (b) conducting high resolution imaging and analysis of the individual elongated nucleic acid molecules on the nucleic acid molecule imaging array.

Labeling of Chromatin and Nucleic Acid Molecules

In any of the foregoing methods and arrays, labeling of the chromatin and nucleic acid molecules can be achieved using any label and labeling technique for genetic and epigenetic studies. Below are some examples of particular labels and labeling techniques, although the present invention is not limited to those described herein.

The chromatin and nucleic acid molecules (referred to collectively as "genetic material" in regard to the labeling disclosure provided herein below) in the sample can be complexed, pretreated, or mixed with one or more labels. In one embodiment, the genetic material is labeled with a plurality of labels, at least one of which is specifically complexed with an epigenetic marker on said genetic material and at least one other label that is complexed with a protein and/or nucleotide of said genetic material. Labels include fluorescent dyes, quantum dots, magnetic particles, metallic particles, and colored dyes. Examples of dyes are described herein. The dyes or labels can be conjugated to binding moieties such as antibodies, nucleic acids, proteins, aptamers, affinity clamps, peptides, naturally occurring proteins and protein domains that bind to target proteins of interest. The binding moieties can be specific or generic. In some embodiments, one binding moiety is specific to an epigenetic marker and a second binding moiety generically binds to nucleic acids, proteins, or biological molecules.

The genetic materials to be analyzed can be analyzed with or without a label. In some embodiments, the genetic material is not labeled and detection techniques not reliant on labels can be used to characterize the genetic material. For example, electrical conductance and UV absorbance can detect DNA in the absence of a label. In other embodiments, the genetic material to be analyzed is labeled such that properties of the genetic material can be observed. Labels can be specific to certain trains of the genetic material, or the labels can be generic. Generic labels include labels that bind non-specifically to nucleic acids (e.g., intercalating dyes, nucleic acid groove binding dyes, and minor groove binders) or proteins. Examples of intercalating dyes include YOYO-1, TOTO-3, Syber Green, and ethidium bromide. In some cases, the method provides alternative approaches to label chromatin, other than YOYO-1 or TOTO-3.

Samples may be labeled with specific labels. Specific labels can include detectable moieties (e.g., dyes, metal particles, radioactive particles, and magnetic particles) that are conjugated to moieties that bind to specific genetic markers. Chromatin may be labeled using such specific labels. Chromatin isolated from embryos at different stages from fertilization to gastrulation can be labeled with a QD-labeled antibody recognizing H3K27me3, H3K4me3 and 5-methylcytidine, or any other known epigenetic marker using a different color QD for each antibody. Alternatively, any suitable labeling reagent may be used to label epigenetic modifications such as a binding agent that specifically recognizes epigenetic markers as provided herein including but not limited to labeled antibodies, antibody fragments, minibodies, affibodies, avimers, aptamers, other proteins that bind epigenetic markers or groups of markers associated with chromatin such as MDB1. Labeled binding agents used herein can complex with any target of interest described herein. Targets of interest can include MBD1, RNA Pol II, RNA, DNA, SWI/SNF, mRNA, pre-mRNA, miRNA, piRNA, lincRNA, and siRNA. Similarly, suitable labels may include but are not limited to QD, organic fluorophores, or agents that can be detected by changes in magnetic or electrical properties. Where desired, the labeled chromatin may be sorted on a device of the present invention and fractions with each combination of these marks may be isolated for subsequent high throughput (e.g. Solexa, Illumina, 454/Roche, etc.) sequencing.

Samples may be labeled with a label conjugated to a binding moiety that complexes with a target. In some embodiments, the target is a specific DNA sequence. Specific DNA sequences can be recognized using labeled binding moieties, such as labeled probes, nucleic acid sequences, and DNA binding proteins. DNA binding proteins include, but are not limited to, those described in Jamieson, Nat Rev Drug Discov 2: 361-8 (2003), Urnov, Nature 435: 646-51 (2005), Moscou, Science 326: 1501 (2009), and Nielsen Science 254, 1497 (1991).

In some instances, two generic dyes and one specific dye corresponding to a first property can be used to label a sample. This can allow for distinction between free dye, objects without the first property, and objects with the first property. In other embodiments, two generic dyes and two specific dyes may be used to label a sample, where the first specific dye corresponds to a first property and the second specific dye corresponds to a second property. In addition to detecting free dye, objects without a first property, and objects with a first property, this would allow for detection of objects without either the first or second property, objects with the second specific property, objects without the second property, and objects with both the first and second property.

Nucleic acid binding agents can be used to label a sample. Non-limiting examples of labels or labeling moieties include probes of a specific sequence, intercalating dyes, and minor groove binders. Generally, fluorescent intercalators can be dyes that bind to double-stranded DNA or double-stranded RNA by inserting themselves in between a neighboring base pair. Generally, minor groove-binders can be dyes that bind to the minor groove of double-stranded DNA. There are still other dyes that may bind to nucleic acids via multiple modes, including electrostatic interaction between a positively charged dye and the negatively charged nucleic acid. In some cases, it is desirable to image all chromatin fragments, regardless of their epigenetic states. For example, one may identify the proportion of sites in the blastocyst genome that carry the H3K27me3 and H3K4me3 epigenetic marks. At least two alternate approaches are available for labeling all chromatin fragments, independent of intercalating dyes. One approach is to label Alexa-coupled nucleotides to the 3' end of each chromatin fragment using terminal deoxynucleotide transferase (TdT). The Alexa fluor chosen may be spectrally distinct from the QDs chosen for the antibodies. This TdT-mediated labeling is not limited by the cross-linking and only depends on a 3'-OH group at the end of each chromatin fragment. Another approach is to label a histone rather than the DNA using antibody recognizing H1 (anti-H1) or one of the core histones. With 80% of the genomic sequences associated with nucleosomes only extremely rare chromatin fragments will remain unlabeled by anti-H1 in preparations of chromatin fragments in the 20,000 bp size range.

Samples can be labeled with QD-anti-methyl-C for detection of methylated DNA. In some cases, methylcytosines directed towards the nucleosome may be inaccessible to QD-anti-methyl-C in cross-linked chromatin. This can provide lower QD fluorescence emissions for a chromatin fragment relative to the same DNA sequence lacking cross-linked proteins. However, linker DNA between nucleosomes may be unaffected by cross linking, so linker DNA is as accessible in purified DNA as in cross linked chromatin. Second, even for DNA wrapped around nucleosomes, less than half of the signal may be lost because methylcytosines extend into the major groove of DNA so access of antibody in solution to the major groove is what determines QD-anti-methyl-C binding to methylated DNA; DNA is wrapped around the external surface of nucleosomes with less than half the major groove surface area in sufficiently close proximity to the histones to exclude the antibody; thus most of the methylcytosines in a nucleosome is accessible to QD-anti-methyl-C. The combined access of methylcytosines in nucleosome-associated DNA and linker DNA to the solution phase may provide adequate signals for sequences containing methylated DNA.

In some cases, methylated DNA in chromatin may be detected by labeling samples with QD-anti-methyl-C that can bind to methylcytosines and QD-anti-H1 or a 5' or 3' end label that can bind to chromatin. This can be used, for example, to label chromatin from cultured ES cells to analyze the chromatin for methylation. Dnmt1 mutant cells may be utilized as an excellent negative control to assess the specificity of the antibody binding to methylcytosine in the context of chromatin. In this case, chromatin can be from wild type and Dnmt1 mutant ES cells, which may be prepared, similar as to in ChIP, using the above-mentioned labels. The methylcytosines labeled using QD-anti-methyl-C and the labeled chromatin may be analyzed on the nanoscale device of the present invention. This method may identify the proportion of fragments bearing methylcytosine marks and the density of those marks in chromatin. A comparison can be made with the data obtained using purified DNA. In some cases, ES and MEF cell chromatin may be labeled using QD-anti-H 3K4me3 and QD-anti-H3K27me3.

In some embodiments, three labels are mixed with the sample. In an exemplary embodiment, the genetic material can be ES and MEF chromatin. A third QD-labeled antibody may be added to the analysis to detect RNA pol II. By combining this antibody with QD-anti-H3K4me3 and QD-anti-H3K27me3, the methods provides for correlating the epigenetic mark placement with a marker for gene expression competency. In addition, the genome may be queried for coincidence of DNA methylation and H3K27me3.

In some embodiments, the sample is processed by the system without removal of free dye and/or free label. The free dye and/or free label can be characterized appropriately by the system by use of time-correlated or simultaneous detection of a plurality of properties. In other embodiments of the invention, free dye and/or free label is removed from the sample prior to sorting. The concentration of the free dye and/or free label in the sample can be about, less than about, or greater than about 0.01, 0.05, 0.1, 0.2, 0.3, 0.4, 0.5, 0.6, 0.7, 0.8, 0.9, 1, 2, 3, 4, 5, 6, 7, 9, 10, 15, 30, 50 times the concentration of the dye and/or label that is complexed with the object or genetic material.

EXAMPLES

The following examples are intended to illustrate particular embodiments of the present invention, but are by no means intended to limit the scope of the present invention.

Example 1

Transfer-Printing of Single DNA Molecule Arrays on Graphene for High Resolution Electron Imaging and Analysis This example describes a new procedure for depositing ordered arrays of individual elongated DNA molecules on single-layer graphene substrates for high resolution electron beam imaging and electron energy loss spectroscopy (EELS) analysis. This demonstrates the capability to observe elemental composition of DNA with sufficient resolution to directly read genetic and epigenetic information with single base spatial resolution from individual elongated DNA molecules.

Methods

Materials.

To prepare phage lambda DNA solution, 100 µl phage lambda DNA solution (Sigma, 48 502 bp, 329 µg/ml diluted to 50 µg/ml in 10 mM Tris-HCl/1 mM EDTA, pH 8) was heated at 65° C. for 5 min and dipped into ice water to avoid molecular concatenation. For fluorescence imaging, the solution was then fluorescently labeled with YOYO-1 intercalator (Invitrogen) by adding 1.5 µl of YOYO-1 (100 µM); incubation was conducted in the dark at room temperature for a minimum of 2 hours. Following the labeling reaction, samples were protected from light and stored at 4° C. Phage lambda DNA solution was further diluted to a final concentration of 10 µg/ml in the same buffer with 0.1% v/v Triton X-100. Note that for electron beam imaging, the DNA molecules were used unlabeled.

TEM grids coated with ultra-thin lacey carbon were purchased from Pacific Grid Tech (San Francisco, Calif.).

Fabrication of Master and Stamps.

To direct the capillary assembly of phage lambda DNA or chromatin, applicants used PDMS stamps with topographical cavities obtained from the replication of a positive silicon master. The silicon micropatterned master was achieved by ultraviolet photolithography and the pattern transfer by deep reactive ion etching. The PDMS prepolymer solution containing a mixture of 10:1 mass ratio of PDMS oligomers and a reticular agent from Sylgard 184 Kit (Dow Corning, Wilmington, Del.) was then poured onto the silicon master and cured at a temperature of 80° C. during 12 hours. The cured PDMS was peeled off and cut into 1 cm×1 cm stamps.

In a general manner, the design of the topographic patterns requires a prior reflexion in terms of distribution, dimension, depth, and orientation. In fact, the size of the patterns determines the number and the positioning of the objects to be assembled for assemblies of controlled geometry. Given the dispersion in size of the objects in solution, the patterns are usually intentionally enlarged to facilitate the assembly by compensating the fluctuations in size among the objects. The depth of the patterns is also a key geometrical parameter to take into consideration as it determines the number of layers to be deposited inside the patterns and ensures the subsequent transfer of the assembled objects. When the stamp is used as support for capillary assembly, the design rule to keep in mind is that the deformation of the liquid contact line has to be minimized in order to avoid its premature disruption, and allow the forces involved to direct and gather the objects at the liquid front line to fill the cavities appropriately. So additionally, the periodicity of the patterns has to be large enough so the contact line can get pinned on each row of patterns without missing one. In the case of DNA molecules' assembly, the silicon master was designed with protruding microfeatures 5 μm and 8 μm in diameter, 5 μm high and with different periodicities (20 μm, and 25 μm). Therefore, the corresponding PDMS stamps are the negatives of the master and consist of microcavities with the same sizes.

Experimental Setup.

The so-called directed assembly is carried out using a dedicated setup. The microstructured PDMS stamp where applicants want the DNA molecules to be assembled is placed on a motorized translation stage below a fixed glass spreader at a distance of about 1 mm. A 15 μl droplet of DNA molecules in solution at a concentration of 10 μg/ml is injected between the glass and the substrate. The liquid contact line is therefore moved over the substrate at a constant velocity of 0.5 mm/sec for the trapped DNA molecules to be stretched. The experiment is conducted at ambient temperature. The experimental parameters (speed, concentration) are adjusted to enable the directed assembly and combing of single DNA molecules with high placement accuracy. The assembly is performed throughout the entire surface of the PDMS stamp, so approximately over an area of more than 1 cm$^2$, allowing the analysis of approximately 1 million molecules over an entire substrate.

Graphene Deposition on SiO$_2$ Surfaces or TEM Grids.

Figure 8:
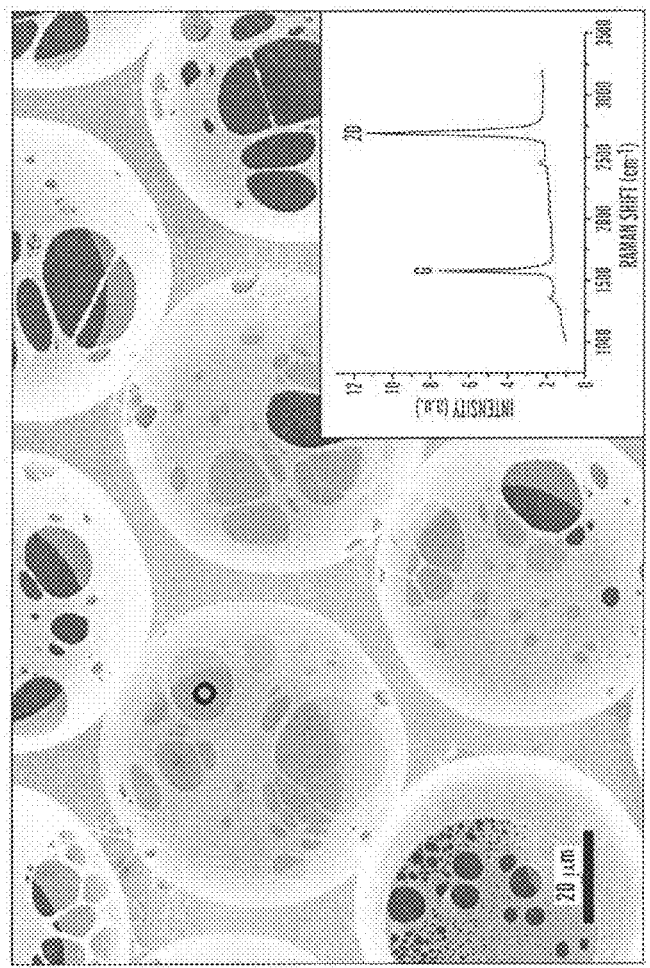
FIG. 8 is a scanning electron microscope image of suspended graphene sheets on TEM grids with ultra-thin lacey amorphous carbon film. The inset graph displays the Raman spectra measured on a suspended graphene sheet. The 2D peak's full width at half maximum is 39 $cm^{-1}$.

Graphene was grown using chemical vapor deposition on copper foils (Li et al., Science 324, 1312-1314 (2009)). It was verified to be predominantly single-layer by Raman spectroscopy (Ferrari et al., Phys. Rev. Lett. 97, 1-4 (2006)). The graphene sheets were then transferred on silicon dioxide substrates or molybdenum TEM grids with lacey carbon support films following the graphene transfer technique developed in (Reina et al., Nano letters 9, 30-35 (2009)). After chemical vapor deposition, a 50 nm-thick poly (methyl-methacrylate) (PMMA) film was spin-coated on the copper foil. Copper was etched in a ferric chloride solution; the graphene/PMMA was then transferred on TEM grids and PMMA was dissolved in a dichloromethane bath for 6 hours (Li et al., Science 324, 1312-1314 (2009); Jiao et al., J. Am. Chem. Soc. Comm. 130, 12612-12613 (2008)). FIG. 8 displays the scanning electron microscope image of single layer graphene suspended over the lacey carbon TEM grids. For AFM imaging, graphene was prepared by mechanical exfoliation (Novoselov et al., Science 306, 666-669 (2004)) and deposited on a freshly cleaned silicon dioxide substrate.

DNA Assembly Transfer.

To transfer the formed DNA arrays, a droplet of solvent (absolute ethanol) is placed on the graphene substrate (graphene on SiO$_2$ or on TEM grids). Ethanol having a low surface tension, it spreads easily creating a thin film of liquid all over the substrate. Ethanol is then left to evaporate, but not fully, and the PDMS stamp with the assembled DNA molecules is then brought into contact with the wet graphene substrate for 2-3 min for the solvent to fully evaporate. The PDMS stamp is then peeled away (FIG. 1).

Imaging.

The molecules' transfer on graphene was controlled under an upright epifluorescence microscope (×20 and ×50 objectives) from Olympus equipped with a 512×512 camera.

AFM imaging. For AFM imaging and measurements applicants used a NanoScope IIIa from Digital Instruments. All imaging was done in tapping mode in air, with a resolution of 512×512 using NC silicon AFM probes (Bruker Company).

STEM and EELS analysis. STEM imaging was performed using a field emission transmission electron microscope with monochromator (Tecnai F20) operated at 200 kV, with a 200 mm camera in dark field mode. EELS mapping was conducted within a 90 eV-1140 eV window, with a 4 seconds acquisition time, and a 0.5 eV dispersion. The resulting map was then filtered at an energy loss of 130 eV using Cornell Spectrum Imager software.

Discussion

Elongation of molecules for direct electron imaging has been an issue that applicants have been addressing. Applicants have shown, for example, that electrospinning of DNA in nanofibers can present individual elongated DNA molecules in a thin support medium for electron beam analysis (Bellan et al., J. Vac. Sci. Technol. B 25, 2255-2257 (2007); Bellan et al., Nano Lett. 6, 2526-2530 (2006)), but the thickness of the supporting medium limits the possibilities for elemental and spatial analysis. The ideal case would be to have no supporting medium, but this is of course not possible. The best possible case would be to have a high-strength, electrically-conducting, single element, low atomic number support on which one could reliable elongate and place molecules. The best candidate for this is single-atom-thick graphene (Geim et al., Science 324, 1530-1534 (2009); Lee et al., Science 321, 385-388 (2008); Meyer et al., Nature 454, 319-322 (2008); Nair et al., Appl. Phys. Lett. 97, 153102-1-153102-3 (2010)). In this example applicants demonstrate a reliable technique for elongating individual DNA molecules and transferring them in ordered arrays to a single-atom-thick mechanical support layers for high resolution scanning transmission electron microscopy and elemental analysis by electron energy loss spectroscopy. This approach satisfies the three requirements mentioned previously and adds the advantage of being able to pre-treat the DNA and create spatial order that can simplify the analysis. While the complexity of the STEM systems limits the throughput and practicality of this approach it demonstrates the possibilities for electron beam analysis of individual biopolymers.

In the present example, applicants present as just one part of the method a technique to transfer regular arrays of individual elongated DNA molecules onto single-layer graphene substrates. This aspect of the method relies on assembling DNA on a microstructured PDMS stamp by capillary assembly. Applicants previously reported this aspect of the experimental procedure (Cerf et al., *Microelec. Eng.* 86, 1419-1423 (2009); Cerf et al., *J. Mater. Res.* 26, 336-346 (2010)) to transfer arrays of single phage lambda DNA molecules from a PDMS stamp to a hydrophilic and positively-charged surface by simple contact in dry conditions. Here, graphene being highly hydrophobic, the transfer is performed with solvent mediation. Applicants obtain regular arrays of single phage lambda DNA molecules adsorbed on graphene following a Poissonian distribution with a 91% success rate (Cerf, A., "Directed Assembly of Nano-Objects," Ph.D. Thesis, Toulouse University (2010)). Applicants prove, for the first time, that subsequent imaging of the assembled molecules is possible using a transmission electron microscope without any prior metallization or labeling of the DNA molecules.

In the so-called directed assembly technique, patterning is used to create a well-defined spatial distribution of forces that direct the motion of molecules in solution towards specific areas of a substrate. In the present case, applicants use a PDMS stamp with topographical features to direct that assembly process. The experimental parameters, namely, the concentration and the displacement speed are chosen to trap and stretch individual molecules. After capillary assembly, the resulting DNA array is transferred onto the graphene substrate. In practice, applicants deposit a droplet of ethanol not fully allowed to dry on the graphene substrate and the PDMS stamp is brought into contact with that wet surface for 2 min. The solvent placed between the PDMS stamp and the substrate during contact mediates the transfer. The PDMS stamp is finally removed, leaving the DNA array on the graphene surface (FIG. 1).

Figure 4A:
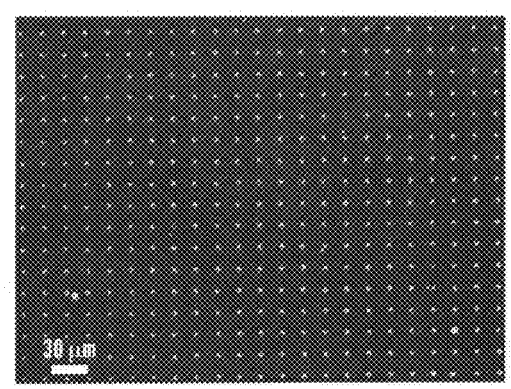
FIGS. 4A-4B are images showing DNA transfer on CVD graphene. Fluorescence images of an array of single nucleic acid stained phage lambda DNA molecules transferred with solvent mediation onto a silicon dioxide surface with single-layer CVD graphene (excitation at 488 nm).
Figure 4B:
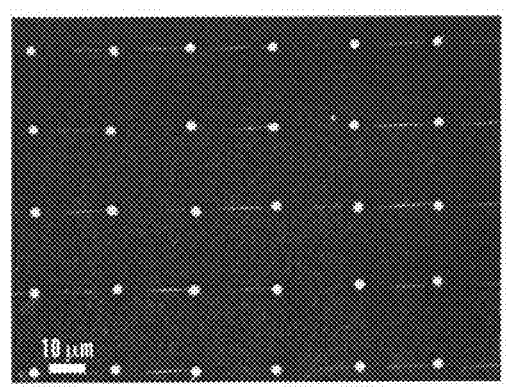

In general, for the transfer to occur, the molecules need to have more affinity for the target surface than for the PDMS stamp's surface. In the present case, the two surfaces are highly hydrophobic (PDMS vents graphene) with a measured contact angle of 108°±2° and 92°±2° respectively, so when the contact is made in dry conditions, the molecules are not naturally transferred from the stamp to the graphene surface. FIG. 4 shows a fluorescence micrograph of individual DNA molecules transferred to CVD graphene on silicon dioxide with solvent mediation. Applicants observe that the transfer is performed reliably over large areas. All the molecules present at the surface of the PDMS stamp are transferred. Furthermore, applicants observe the presence of periodic fluorescent spots that correspond to the material initially contained in the PDMS wells during capillary assembly. The transfer method is so effective that even the material trapped and not directly in contact with the surface is transferred.

However, not all liquids or solvents are proper to transfer the assemblies from a PDMS stamp onto a substrate. In the present case, the category of good solvents such as trichloroethylene, hexane, toluene are to be excluded as they irreversibly deform and damage the PDMS stamp, and are not compatible with biology in a more general manner. In this regard, water could have been a candidate to consider, but its surface tension in the presence of a hydrophobic surface prevents the creation of a thin layer of liquid and prevents the PDMS stamp from contacting the surface in a conformal manner as well. Consequently, applicants suggest different hypotheses concerning the influence of ethanol. On the one hand, compared to ethyl acetate for example, ethanol only exerts a swelling extent of 6.3% on a weight basis of bulk PDMS (Favre, E., *Europ. Polym. Jour.* 32, 1183-1188 (1996)). But this swelling may modify in some manner the PDMS features and facilitate the release of the assembled molecules. On the other hand, during contact of the stamp with the substrate, in liquid, the evaporation process may lead to the creation of capillary forces that direct the elongated molecules towards the wetting target surface. Thus, the natural evaporation process may facilitate the release of the trapped and elongated molecules. However, it is still difficult to know which one of these candidates is responsible for molecule transfer.

Figure 5B:
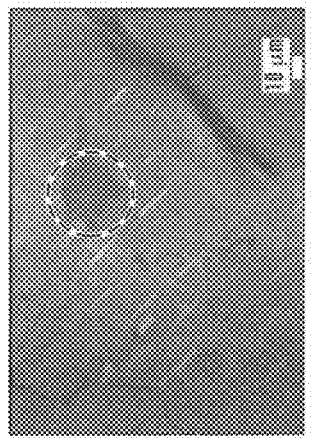
FIGS. 5A, 5B, 5C, 5D are images showing DNA transfer on exfoliated graphene. Bright field (FIG. 5A), fluorescence (FIG. 5B) and atomic force microscope (FIG. 5C) images of the same area of a substrate after transfer of nucleic acid stained DNA molecules onto a silicon dioxide wafer with exfoliated graphene.
Figure 5A:
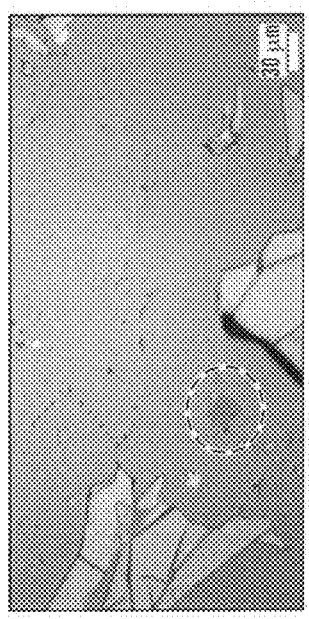
Figure 5C:
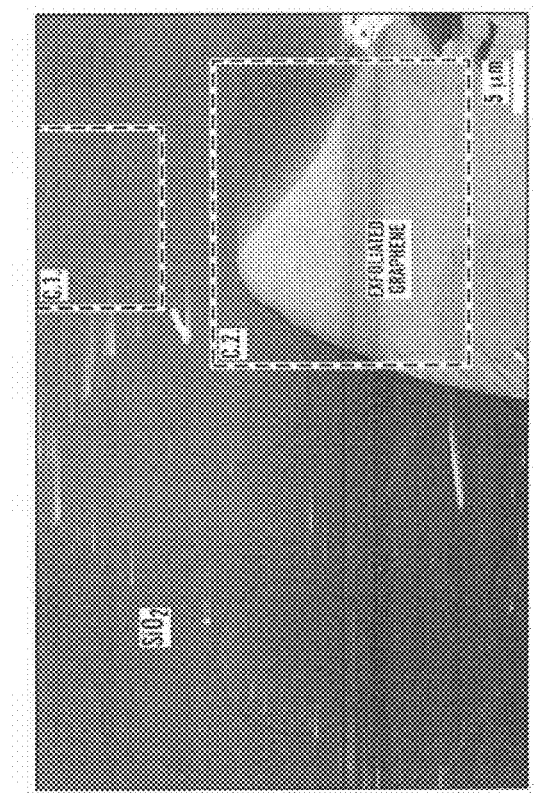
Figure 5D:
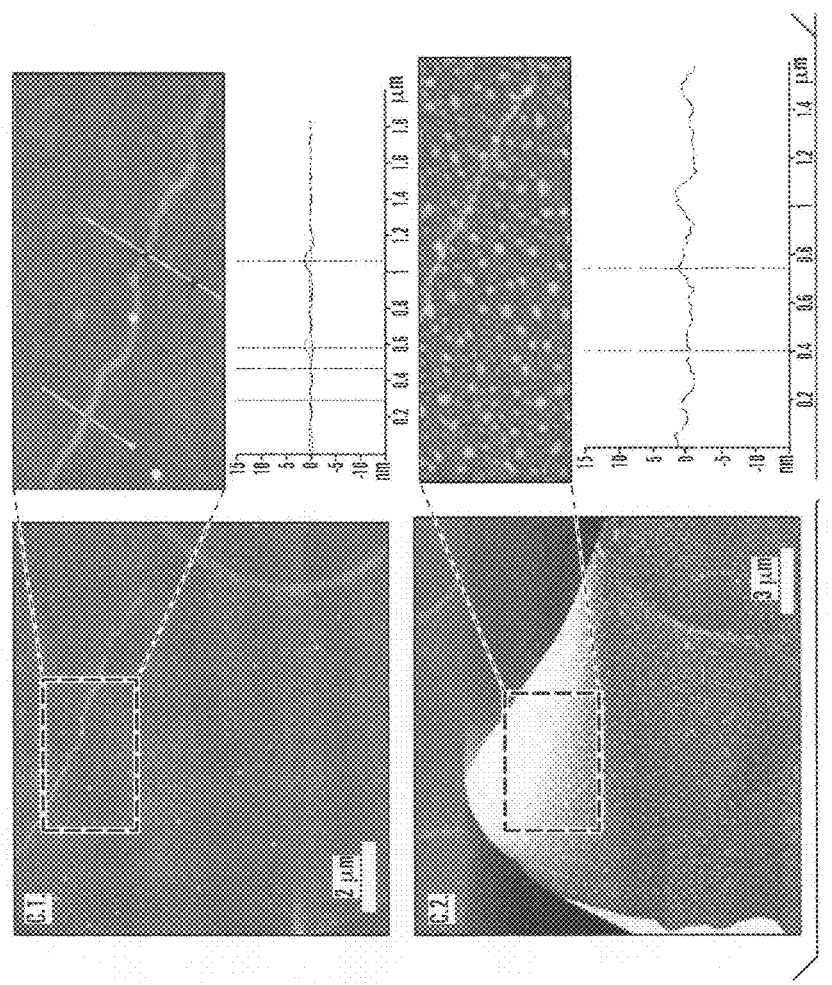

Applicants also notice that the fluorescence intensity of YOYO-1 intercalated DNA molecules on graphene is somewhat lower than the fluorescence intensity one could obtain with molecules transferred onto glass. This suggests that there is a certain degree of quenching provoked by graphene, in agreement with previous results (Kim et al., *J. of the Am. Chem. Soc.* 132, 260-267 (2010)). This, however, does not prevent the characterization of molecules using fluorescence microscopy. To further demonstrate that the DNA array is composed of individual molecules, applicants performed the transfer on exfoliated graphene for AFM imaging. The presence of residual iron particles ~10 nm in diameter on the CVD graphene after its transfer to silicon dioxide inhibits the proper characterization of individual molecules with such a technique. Thus applicants chose exfoliated graphene, well-known for its atomically-flat surface as our substrate for AFM imaging purposes. FIG. 5 shows a bright field, fluorescence and AFM image of the same area of a silicon dioxide substrate with exfoliated graphene after transfer of a DNA array. In the bright field image applicants observe the presence of the PDMS stamp feature imprints. In the fluorescence image, FIG. 5B, the elongated DNA molecule which is part of the array and positioned on the exfoliated graphene is not visible possibly due to quenching. However, its presence can be detected by AFM. FIG. 5D (top row) shows an enlarged image of a DNA molecule on silicon dioxide. From the corresponding cross-section applicants observe that it is a single molecule measuring 1.57 nm in height. FIG. 5D (bottom row) shows a magnified image of a DNA molecule on exfoliated graphene. In contrast to the measurement on silicon dioxide, the roughness is comparable to the height of the molecule (2 nm on average). Applicants attribute this roughness to impurities attracted to exfoliated graphene during the transfer process that we do not observe on silicon dioxide. The measurements from the different AFM and fluorescence images show that the DNA molecules measure in average 16.3 µm±4.4 µm long, which is approximately equal to the theoretical length of individual phage lambda DNA molecules (Smith et al., *Macromolecules* 29, 1372-1373 (1996)).

Figure 6A:
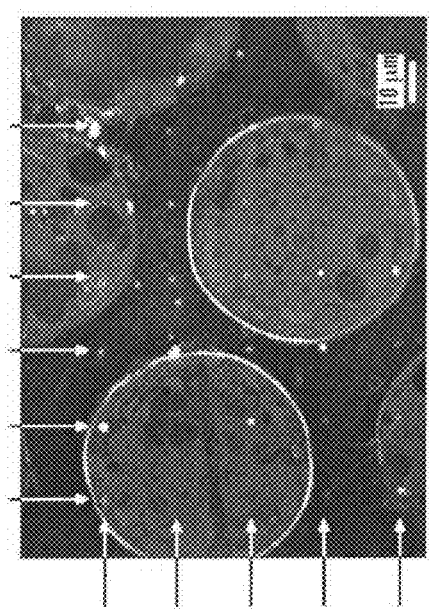
FIGS. 6A-6D are images showing DNA transfer on TEM grids with suspended graphene.
Figure 6B:
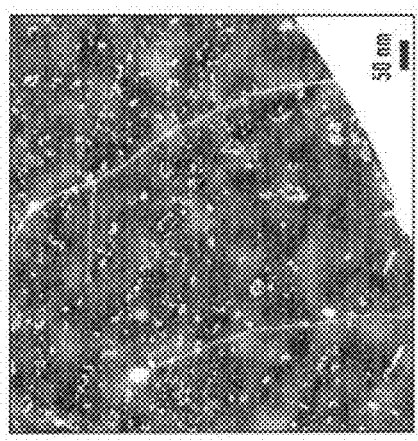
Figure 6D:
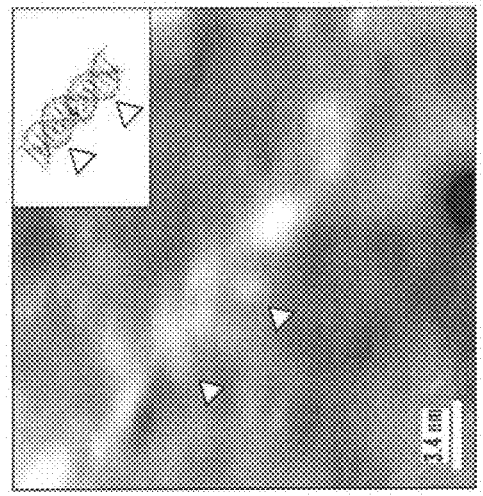
Figure 6C:
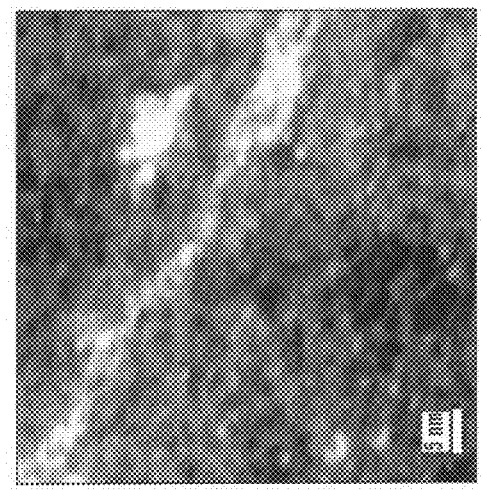

By extension, the transfer process can be performed on any type of graphene substrates such as TEM grids with lacey carbon support films. In this case, commercial molybdenum TEM grids pre-coated with a web of amorphous carbon fibers (lacey carbon) are used as a support to suspend atomically-thick graphene films. FIG. 6A shows a fluorescence image of nucleic acid-stained DNA molecules transferred on this type of grid. From this image applicants recognize the bright spots corresponding in periodicity to the patterns of the PDMS stamp. However, single molecules are not visible by fluorescence as the autofluorescence of the grid is much higher than that of silicon dioxide. FIGS. 6B, 6C, and 6D show the transmission electron micrographs obtained from DNA elongated and adsorbed on lacey carbon grids with suspended graphene. Note that no plasma treatment or heating step was required prior to imaging. First, applicants observe that the images show little charging or contamination. This implies that applicants' methodology as a whole is very clean and adapted to high resolution imaging purposes. Second, applicants observe that suspended single-layer graphene sheets remain on the grid after transfer, so the forces exerted during PDMS peel-off are low enough to prevent graphene from rupturing. Third, while DNA could not be imaged using standard TEM grids without prior labeling, on single-layer graphene TEM grids DNA can be characterized with no difficulties and long exposure times. DNA appears to be undamaged after transfer, measuring 2-3 nm wide in the case of single molecules. If applicants compare the outside region of the lacey carbon and the inner area (FIG. 6B), applicants can see that the contrast in the presence of suspended graphene is much higher. FIGS. 6C and 6D show higher magnification micrographs of the region shown in FIG. 6B, where the molecule seems to present a B conformation with a 4.6 nm pitch. The periodicity of the double-helix is in this case 1.35 times greater than the theoretical pitch reported by Watson and Crick (Watson et al., *Nature* 171, 737-738 (1953)), but these observations seem consistent with the ones reported in literature in similar conditions (Fujiyoshi et al., *Ultramicroscopy* 7, 189-192 (1981); Inaga et al., *J. Electron Microsc.* 40, 181-186 (1991); Arnott, S., *Nature* 278, 780-781 (1979)). Instead of considering the inelastic energy as a whole, the spectral distribution of the forward scattered electrons can be analyzed separately. A highly specific signature lies in the characteristic core-loss edges: their energy position corresponds to a given atomic level and therefore identifies a given element within the irradiated volume.

Figure 7C:
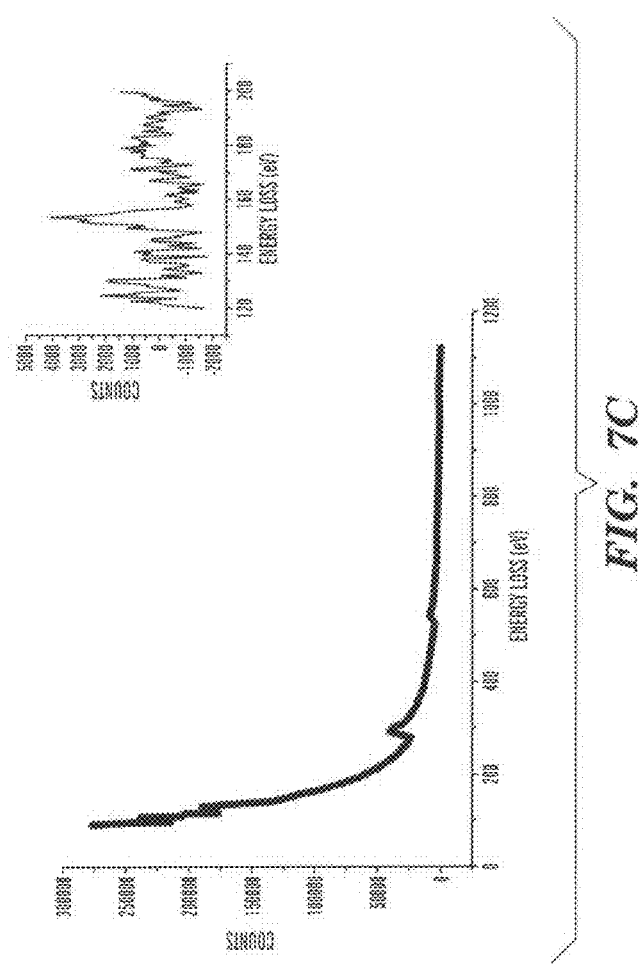

A way of exploiting electron energy loss spectroscopy (EELS) is to produce images representative of elemental distribution by scanning the probe, recording several energy-filtered images on both sides of the core-loss edge, and processing them pixel by pixel display maps of the resulting characteristic signal. Applicants know that the support is constituted by a molybdenum lacey-carbon grid and graphene, both composed primarily of molybdenum, iron, and carbon elements. Applicants selected an area with elongated DNA molecules as shown by the bright field image (FIG. 7A), and applicants recorded a 20×20 EELS mapping with a 4 seconds acquisition time per pixel. Interested in obtaining a characteristic signature of DNA, applicants then filtered the resulting map at an energy-loss of 130 eV corresponding to the edge of phosphorous. Although the total acquisition time was close to 1 hour, the specimen remained stable and no noticeable change of the phosphorous energy loss signal was observed. The presence of phosphorous is observed all along the molecule (FIG. 7B). This suggests that phosphorous can be used as an indicator of individual bases. If the DNA molecule can be formed with non-native elemental labels on the different bases, the energy filtered images can reveal the base sequence. As shown in FIG. 7C, applicants notice from the accumulated spectra extracted from the entire map without energy filtering, the K edges of carbon (285 eV), nitrogen (400 eV) and oxygen (532 eV) as expected. Applicants see at around 130 eV the $L_{23}$ edge of phosphorous corresponding to the excitation of 2p electrons. Note that in that range, applicants also observe the $L_{23}$ edge of silicon (99 eV) more likely coming from PDMS residues during transfer.

By combining directed assembly on a PDMS stamp and microcontact printing with solvent mediation, applicants benefit from the advantages of both techniques at the same time: the control over the assembly process and the flexibility and simplicity of the printing technique. This printing method can handle single objects while preserving their intrinsic properties. It is adaptable to parallel processing over various hydrophilic/hydrophobic substrates and over large areas. In particular, the transfer on graphene opens a wide horizon of possible applications and could be an invaluable technique in MEMS/NEMS technologies but also to allow high resolution imaging of single DNA molecules using electron microscopy in a regular basis for applications in epigenetic and genetic analysis.

By extension, we envision using this protocol to transfer base-labeled DNA and elongated chromatin with energy-loss resolved epigenetic labels. With this process, one can obtain a complete genetic and epigenetic map from individually selected chromosomes without the need for polymerase chain reaction. A STEM is not designed to be a cost-effective sequencing system, however, the possibility for directly reading single molecule information with the spatial resolution of electron beams is possible.

Example 2

Single DNA Molecule Patterning for High-Throughput Epigenetic Mapping

This example describes a new method for profiling the 5-methyl cytosine distribution on single DNA molecules. Our method combines soft-lithography and molecular elongation to form ordered arrays estimated to contain more than 250 000 individual DNA molecules immobilized on a solid substrate. The methylation state of the DNA is detected and mapped by binding of fluorescently labeled methyl-CpG binding domain peptides to the elongated dsDNA molecules and imaging of their distribution. The stretched molecules are fixed in their extended configuration by adsorption onto the substrate so analysis can be performed with high spatial resolution and signal averaging. We further prove this technique allows imaging of DNA molecules with different methylation states.

In this example, we present a method for transferring regular arrays of individual elongated DNA molecules onto $SiO_2$ substrates for optical analysis. In this method, the DNA molecules are labeled with fluorescent MBD1 probes to reveal the methylation sites. As a test of our technique, we used in vitro methylated phage-lambda DNA molecules. In order to map methylation site position, DNA is elongated by capillary forces and organized on a topographically patterned substrate. The elongated molecules are arrested in their extended configuration by transfer-printing on a surface for subsequent high-throughput optical analysis. We show that the spatial location of methylated sites within the molecules can easily be imaged and mapped. Our approach is also consistent with emerging techniques capable of optically mapping the lengths of enzymatically cleaved DNA fragments.

Methods

Preparation of Biological Materials

Core members of the MBD protein family (MeCP2, MBD1, MBD2, and MBD4) share a methyl-CpG-binding domain that has a specific affinity for methylated CpG sites in double-stranded DNA. Here, to assess global levels of DNA methylation, we used MBD1 peptide as our probe, which has been shown to preferentially bind a symmetrically methylated CpG motif (Hendrich et al., *Mol. Cell. Biol.* 1998, 18, 6538-6547). The phage lambda DNA solution (Sigma, 48 502 bp, 329 μg/mL) was heated at 65° C. for 5 min and dipped into ice water to avoid molecular concatenation. Methylation of lambda DNA (Sigma Aldrich) was performed using CpG methyltransferase (M.SssI) from New England Biolabs (NEB) according to their standard protocol. SssI can methylate all 3113 CpGs in the 48.5 kbp genome which are evenly distributed throughout the entire molecule (approximately one CpG island every 16 basepairs). The methylation state was controlled with a methylation-sensitive cleavage of DNA (MspI, NEB) and verified by an electrophoresis gel.

MBD1 Peptide Labeling

MBD1 peptide was purchased from Abcam (Ab4918). Peptides were labeled with Alexa Fluor 488 carboxylic acid, TFP ester (A-10235, Invitrogen), which targets primary amines. The buffer pH was kept close to neutral (pH 7.4) to achieve more specific labeling of the amine terminus. Labeled peptides were purified by gel filtration (Superdex Peptide 10/300 GL, GE Healthcare, 17-5176-01) using an ÄKTA FPLC system (GE Healthcare). The Alexa Fluor 488 labeled MBD1 retained its specificity for methylated DNA.

Methylated and nonmethylated lambda DNA (Sigma Aldrich) were incubated against Alexa488 MBD1 to determine the specificity of the peptide against the methylated binding sites. Methylated and nonmethylated lambda DNA were diluted in 10 mM Tris-HCl/1 mM EDTA, pH 8, to 100 µg/mL. In total, 1 µg each were incubated in molar excess with a 2-fold concentration of Alexa488-labeled MBD1 relative to the concentration of CpG sites in the DNA. Incubation was conducted for 2 h in the dark, at room temperature. Each solution was then counter-stained with BOBO-3 intercalating dye (Invitrogen) at a 1:5 dye per base pair ratio during 2 h in the dark at room temperature. Finally, equal volume of formalin with 0.1% v/v Triton-X100 was added and cross-linking was conducted for 2 min.

Chemical Functionalization of Glass Substrates

The glass coverslips were coated with (3-aminopropyl) triethoxysilane (APTES; Sigma Aldrich 440140) molecules. The chemical functionalization was carried out by immersion of the substrates into a freshly prepared solution containing APTES molecules diluted at 1% with ethanol for 15 min; the slides were then rinsed with ethanol, dried under nitrogen stream, and heated on a 140° C. plate for 5 min.

Operational Procedure

Figure 9:
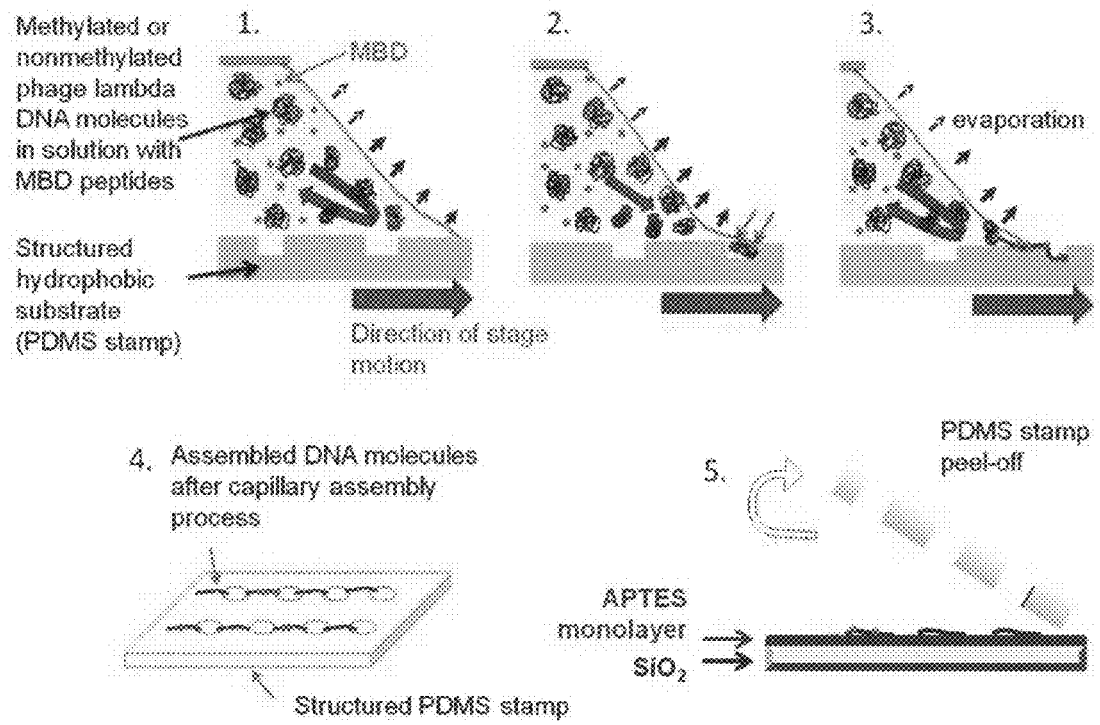
FIG. 9 is a schematic representation of the experimental procedure to generate the DNA arrays for assessment of DNA methylation. Images 1, 2, and 3 represent the capillary assembly process. The liquid meniscus of solution containing fluorescently-labeled MBD1 probes and methylated and/or nonmethylated DNA molecules is dragged over a microstructured PDMS stamp. The molecules are physically trapped and elongated as the meniscus is displaced across the substrate. Images 4 and 5 represent transfer-printing of the DNA array on an APTES-coated coverslip. The PDMS stamp with the DNA array is contacted with the APTES-coated coverslip for 2 mins and then peeled away.

To direct the capillary assembly of phage lambda DNA, we used polydimethylsiloxane (PDMS) stamps with topographical cavities obtained from the replication of a positive silicon master. The silicon micropatterned master was achieved by ultraviolet photolithography and the pattern transfer by deep reactive ion etching. The PDMS prepolymer solution containing a mixture of 10:1 mass ratio of PDMS oligomers and a reticular agent from Sylgard 184 Kit (Dow Corning, Wilmington, Del.) was then poured onto the silicon master and cured at a temperature of 80° C. during 2 h. The cured PDMS was peeled off and cut into 1.8 cm×1.4 cm stamps. In a general manner, the design of the topographic patterns requires a prior reflection in terms of distribution, dimension, depth, and orientation. For DNA molecules' assembly, the silicon master was designed with protruding microfeatures 5 and 8 µm in diameter, 5 µm high and with different periodicities (15 µm, 20 µm, and 25 µm). Therefore, the corresponding PDMS stamps are the negatives of the master and consist of microcavities with the same sizes. The directed assembly is carried out using a dedicated setup. The microstructured PDMS stamp where we want the DNA molecules to be assembled is placed on a motorized translation stage below a fixed glass spreader at a distance of about 1 mm. The experiment is conducted at ambient temperature. A 15 µL droplet of the final DNA molecules' solution is injected between the glass and the substrate. The liquid contact line is then moved over the substrate at a constant velocity of 0.5 mm/s for the trapped DNA molecules to be stretched. The assembly is performed throughout the entire surface of the PDMS stamp, so approximately over an area of more than 1 cm$^2$. To transfer the formed DNA arrays, the PDMS stamp with the assembled DNA molecules is then brought into contact with a (APTES)-coated coverslip for 2-3 min. The PDMS stamp is then peeled away (FIG. 9). The molecules' transfer was controlled under an inverted epifluorescence microscope (100× oil immersion objective) from Olympus coupled to a 512×512 CCD camera (Photometrics). The samples were imaged under illumination at 475 and 560 nm accordingly with no cross-excitation detectable at 535 nor 645 nm. Green and red images were combined using ImageJ software.

Results and Discussion

In the directed assembly technique, patterning is used to create a well-defined spatial distribution of forces that direct the motion of molecules in solution toward specific areas of a substrate. In our case, we use a PDMS stamp with topographical features to direct that assembly process. The experimental parameters, namely, the sample concentration and the displacement speed have been adjusted to enable the trapping and stretching of individual DNA molecules with high placement accuracy as previously reported (Cerf et al., J. Mater. Res. 2011, 26, 336-346). After capillary assembly, the resulting DNA array is immediately transferred onto the APTES-coated coverslip (FIG. 9). In general, for the transfer to occur, the molecules need to have more affinity for the target substrate than for the PDMS stamp's surface. In the present case, the target substrate is hydrophilic (PDMS vs APTES, with a measured contact angle of 108°±2° and 61°±2° respectively) so the transfer is performed reliably. We obtain regular arrays of single phage lambda DNA molecules adsorbed on APTES-coated substrates following a Poisson distribution and with a 91% coverage rate (Cerf, A., "Directed Assembly of Nano-Objects," Ph.D. Thesis, Toulouse University, 2010). First, as a control experiment, we incubated nonmethylated BOBO-3 stained lambda DNA against Alexa488-labeled MBD1 peptides. As MBD1s are CpG-pattern-specific, no binding should occur. FIGS. 10A-10I show the results after capillary assembly and transfer. If we consider the first row of panels of FIG. 10, at 645 nm (FIG. 10A), the fluorescence micrograph shows the presence of a regular array of individual BOBO-3 stained DNA molecules.

Figure 10:
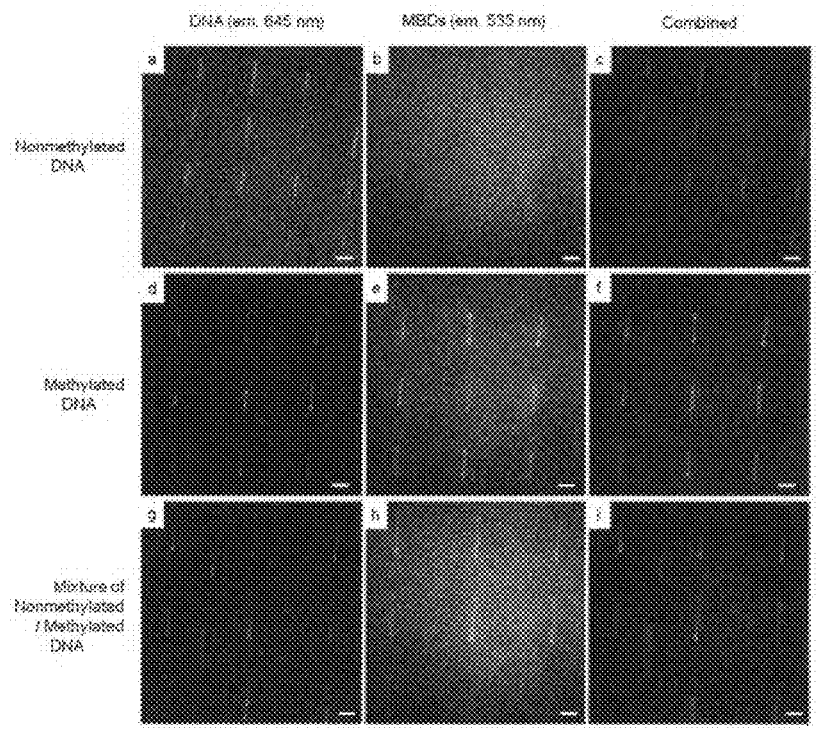
FIGS. 10A-10I are fluorescence micrographs showing an assessment of DNA methylation using capillary assembly. Fluorescence micrographs of elongated methylated and/or nonmethylated BOBO-3 labeled lambda-DNA molecules incubated against methylation-sensitive Alexa488-labeled MBD1 peptides. The first column and second column correspond to fluorescence micrographs taken at 560 nm (emission at 645 nm) and at 475 nm (emission at 535 nm), respectively. The third column corresponds to the composite image resulting from the false color overlay of the first column (red) and the second column (green) micrographs for each case of figure. First row (FIGS. 10A, 10B, 10C): Control experiment using nonmethylated DNA molecules. Second row (FIGS. 10D, 10E, 10F): Methylated DNA molecules. Third row (FIGS. 10G, 10H, 10I): 1:1 mixture of methylated and nonmethylated DNA molecules. For each row, the fluorescence micrographs were taken from the same area. Scale bars correspond to 4 µm.

We notice that DNA molecules are homogeneous in length 10.37±1.60 µm and orientation. We observe in FIG. 10B that at 535 nm, no binding of MBD1 peptides is perceivable as expected. Consequently, the resulting overlay FIG. 10C is the equivalent of the fluorescence micrograph at 645 nm as there is no contribution from the image at 535 nm. Now, the second row in FIG. 10 shows the experiment of interest where in vitro methylated lambda DNA molecules are incubated against Alexa488-labeled MBD1 peptides, assembled, and transferred onto an APTES-coated coverslip. We observe that this time, contrary to the first row of FIG. 10, the DNA array is visible at 645 nm but also at 535 nm. The overlay FIG. 10F of the images taken at 645 nm (FIG. 10D) and at 535 nm (FIG. 10E) shows high-degree colocalization of MBD1 to methylated DNA. This suggests homogeneous MBD1 binding all along the individual molecules as predicted by the dense methylation pattern of the methylated DNA substrates (one CpG island every 16 basepairs so nonmethylated domains are imperceptible). This proves that MBD1 binds specifically to methylated DNA and that the spatial location of binding sites within the molecule can easily be mapped. Here again we determined the length of the molecules based on the images taken at 645 nm (BOBO-3 nucleic acid stained). We observe that MBD1-bound methylated lambda DNA consistently stretches to a length of 10.56±1.16 µm, the same as nonmethylated lambda DNA molecules. Regardless of their methylation state, molecules undergo the same stretching factor as length distributions from methylated and nonmethylated DNA are both centered around 10 µm. Thus the stretching of lambda DNA molecules seems to be independent from the methylation state or pattern. We do not observe any shortening or contraction upon MBD binding unlike the previous report (Lim et al., *Biomicrofluidics* 2011, 5, 034106). We do observe the length distribution is slightly broader in the case of nonmethylated DNA, but we attribute this to a sampling effect rather than an influence of MBD1 binding onto the assembly mechanism. The third row of FIG. 10 shows the resulting DNA array obtained when mixing in bulk methylated and nonmethylated DNA at a 1:1 ratio along with Alexa488-labeled MBD1 peptides. We observe that some molecules are only visible at 645 nm (FIG. 10G) and others are visible in the two panels (at 645 nm (FIG. 10G) and 535 nm (FIG. 10H)), implying that Alexa488-labeled MBD1 peptides have only bound to some of the DNA molecules, revealing the methylated DNA population from the nonmethylated population. In FIG. 10I, the overlay shows an equal proportion of red-colored molecules and yellow-colored molecules, resulting from green and red colocalization in the false-colored image overlay. Since both methylated and unmethylated molecules are elongated, linearized, and aligned the same way, this suggests that the assembly mechanism is independent of methylation state and solution complexity.

Our technique allows elongating and organizing individual molecules on a solid support. One of its major advantages is that the labeling of the molecules with specific antibodies or enzymes can be performed either in bulk or directly on the surface after transfer. If the experimenter chooses to perform it in bulk, as the capillary assembly is conducted at high speed on a highly hydrophobic substrate (PDMS stamp), only the DNA molecules are physically trapped and elongated, while the rest of the solution is dragged over the substrate without being deposited. Since assembly only occurs on the long-chain polymer strands of DNA, this method inherently removes free-dye or other contaminants. We obtain, as a result, regular arrays of individual molecules over more than 1 cm$^2$ in a reliable manner, so approximately 250,000 molecules over the entire substrate that are potentially analyzable. We have proven that we can image and map methylation upon binding of fluorescently labeled MBD1s. The elongated molecules are arrested in their extended configuration by adsorption on the substrate so analysis or detection can be performed with high spatial resolution and signal averaging. From that perspective, there has been a growing interest in using methods to analyze single molecules with spatial resolution beyond the optical diffraction limit while benefiting from the advantages of established fluorescence spectroscopy techniques. As this methodology can be used on various hydrophilic supports, it is compatible with all characterization methods including fluorescence microscopy (TIRF, PALM, STORM . . . ), atomic force microscopy, but also electron microscopy techniques. In fact, this technique is not only adaptable to parallel processing over various hydrophilic substrates but also hydrophobic substrates such as graphene.

We have recently shown that we can transfer arrays of elongated DNA molecules onto single-layer graphene (Cerf et al., *Nano Lett.* 2011, DOI: 10.1021/nl202219w), opening the possibility for single-nucleotide resolution imaging of individual base-labeled DNA molecules or chromatin using transmission electron microscopy (TEM) and electron energy loss spectroscopy (EELS).

In summary, we demonstrate an affordable and fast technique to assess methylation patterns of CpG dinucleotides in single DNA molecules. With the combination of directed assembly on a PDMS stamp and microcontact printing, we benefit from the advantages of both techniques at the same time: the control over the assembly process and the flexibility and simplicity of the printing technique. This ability to controllably pattern large numbers of DNA molecules over large areas offers the opportunity for parallelized and high-throughput screening with high-resolution capabilities. In addition to research use, this simple and fast technique may prove to be especially useful for clinical studies as the procedure is straightforward and does not require complex fabrication or preparation protocols. Further development will lead us onto high-resolution optical imaging (PALM/STORM) to perform high-throughput genetic and epigenetic mapping of DNA with sub-20 nm resolution allowing multiple fluorescent labels to be spatially separated and resolved in the case of multilabeled DNA molecules or chromatin. This may permit molecular mapping and analysis with spatial resolution sufficient to identify multiple epigenetic marks on a single nucleosome or to distinguish marks on adjacent nucleosomes in native chromatin.

Example 3

Ordered Arrays of Native Chromatin Molecules for High-Resolution Imaging and Analysis Individual chromatin molecules contain valuable genetic and epigenetic information. To date, there have not been reliable techniques available for the controlled stretching and manipulation of individual chromatin fragments for high-resolution imaging and analysis of these molecules. We report the controlled stretching of single chromatin fragments extracted from two different cancerous cell types (M091 and HeLa) characterized through fluorescence microscopy and atomic force microscopy (AFM). Our method combines soft-lithography with molecular stretching to form ordered arrays of more than 250,000 individual chromatin fragments immobilized into a beads-on-a-string structure on a solid transparent support. Using fluorescence microscopy and AFM, we verified the presence of histone proteins after the stretching and transfer process.

We present a method for the stretching of chromatin molecules into ordered arrays on solid platforms compatible with scanning probe and optical imaging techniques. The controlled stretching of chromatin enables high-throughput location-resolved optical investigation of DNA and nucleoproteic material with a resolution set by signal averaging and the imaging technique employed. This level of single-molecule analysis is important to identify spatial relationships among chromatin features which provide insights into regulatory processes controlling normal chromatin states and how they are disrupted in disease, for studying epigenetic variability in mammalian heterogeneous samples, but also for fundamental understanding of biological processes in non-mammalian organisms such as drosophila.

Methods

Preparation of Biological Materials

Chromatin Extraction.

Figure 15:
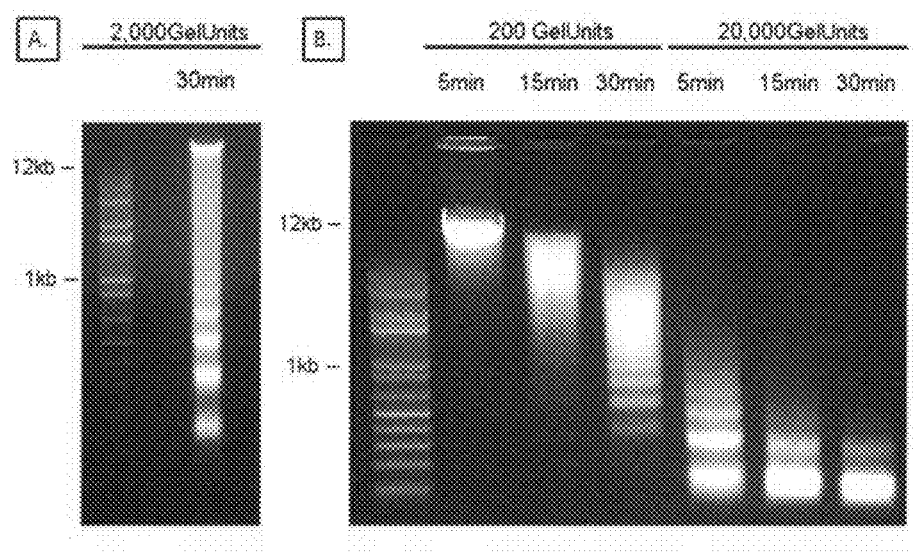
FIGS. 15A-15B illustrate electrophoresis gels from M091 (FIG. 15A) and HeLa (FIG. 15B) chromatin extractions. Above each gel, the upper bars indicate micrococcal nuclease concentration and the digestion times associated with each lane.

Acute myelogenous leukemia-derived cells (M091) (Scandura et al., *PNAS.* 2004, 101, 15231-15236) were cultured as a suspension in Dulbecco's modified Eagle's medium (DMEM) supplemented with 5% fetal calf serum at a density of $10^5$ cells/ml. HeLa cells were cultured as monolayers in DMEM supplemented with 5% fetal calf serum. HeLa cells were plated at a density of $10^5$ cells per plate. When the cells reached 80-90% confluence, native chromatin fragments were extracted as described (Ersfeld, K., *Meth. in Mol. Biol.* 2004, 270, 395-402). Micrococcal nuclease (NEB M0247S) digestion times were set to 30 min (2000 gel units) and 5 min (200 gel units) for M091 and HeLa chromatin respectively. Extracted chromatin was resuspended in a final buffer of 10 mM EDTA and 0.5M NaCl. The resulting fragment size distribution of extracted chromatin was evaluated through an electrophoresis gel (see FIGS. 15A-15B).

Extracted chromatin was stained with YOYO-1 (Invitrogen, 100 µM) at a 1:5 dye/base ratio for control experiments.

Antibody Labels.

Histone H3 monoclonal antibodies (39763) were purchased from Active Motif. Alexa 647 goat anti-mouse secondary antibodies were purchased from Invitrogen. Both primary and secondary antibodies were used at 1:200 dilution.

Histone Labeling.

2 µg of M091 or HeLa chromatin were separately incubated against histone primary antibodies for 1 hour at room temperature. Secondary antibodies were then added to the solution in equal proportion as primary antibodies and incubated for an additional 30 min at room temperature. The entire solution was then counter-stained with YOYO-1 intercalating dye (Invitrogen) for a minimum of 30 min in the dark at room temperature. Finally, 15 µl of 1× PBS with 0.3% Triton X-100 v/v were added to adjust the contact angle of the solution with respect to the PDMS surface (measured contact angle of 45° in water). The total volume was used for each directed assembly experiment.

Operational Procedure.

Figure 11:
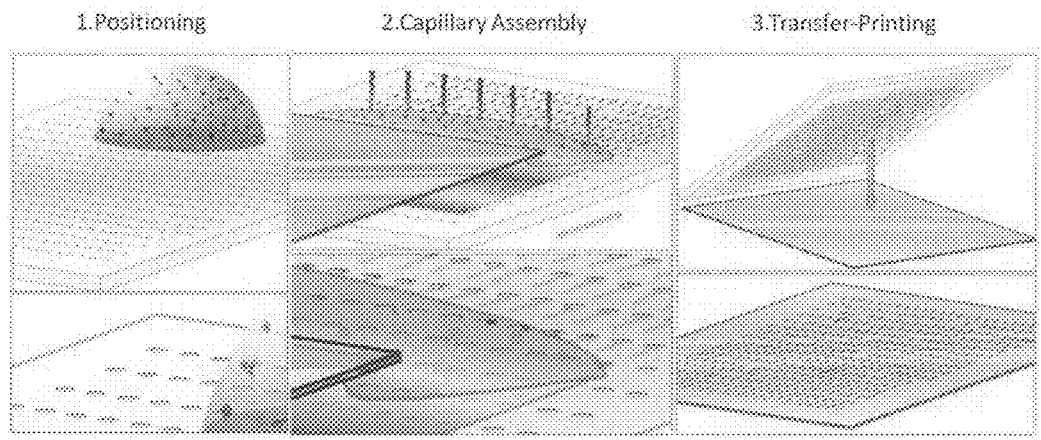
FIG. 11 is a schematic representation of the experimental methodology to generate stretched and oriented chromatin arrays on a solid support. (1), and (2) represent the assembly and stretching process by capillarity. (1) The microstructured PDMS stamp is placed on a translation stage controlled in speed. A droplet of extracted chromatin in solution is deposited on the stamp. (2) The liquid meniscus of the solution containing the extracted chromatin is dragged over the microstructured PDMS stamp at controlled speed. The molecules are physically trapped and stretched as the meniscus is displaced across the substrate. The evaporation phenomenon is represented in red. (3) represents the transfer-printing of the obtained chromatin array on an APTES-coated cover slip by contacting the PDMS stamp with the APTES-coated surface for two minutes and then peeling it away.
Figure 17:
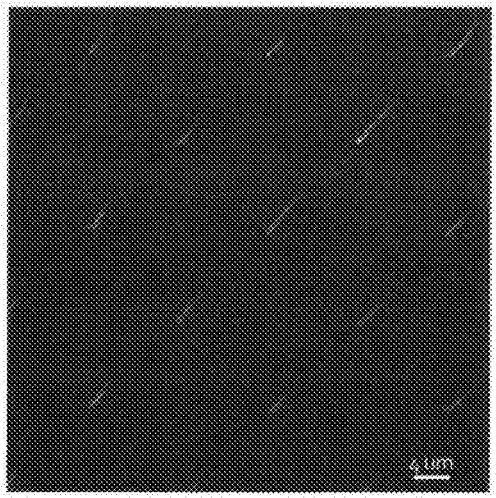
FIG. 17 illustrates a HeLa chromatin array. Fluorescence image of an array of stretched and oriented HeLa chromatin molecules transferred onto an APTES-coated cover slip (excitation at 475 nm). The molecules are YOYO-1 stained.
Figure 18:
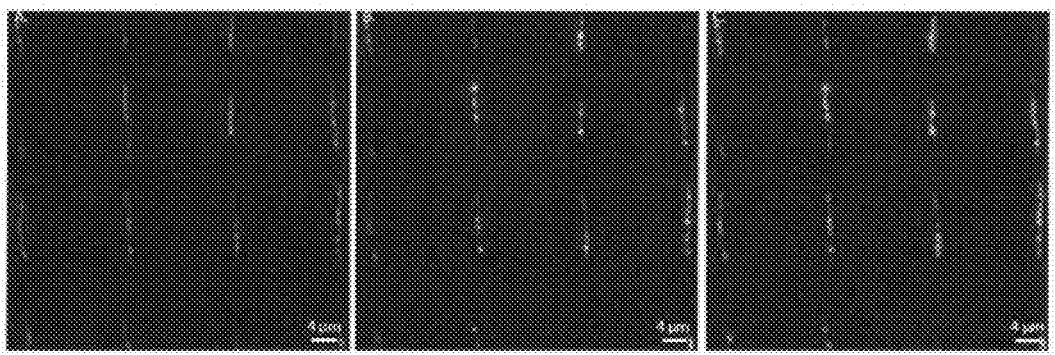
FIGS. 18A-18C illustrate HeLa chromatin arrays labeled with Alexa 647-labeled histone H3 antibodies. DNA is stained with YOYO-1.
Figure 19:
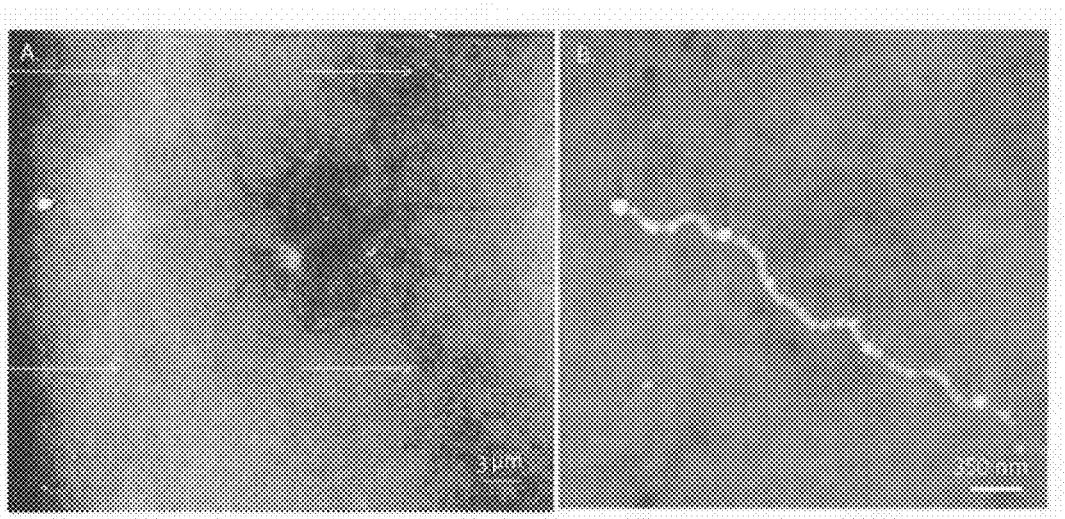
FIGS. 19A-19B are AFM images of HeLa chromatin arrays.

To direct the capillary assembly of digested chromatin, we used PDMS stamps with topographical cavities obtained from the replication of a positive silicon master. Conventional photolithographic techniques (proximity UV lithography) and reactive ion etching (RIE) were used to fabricate a silicon master with the negative of the final desired micropatterns. The design consists in arrays of 5 µm and 8 µm in diameter, 5 µm high protruding features, with different periodicities (15 µm, 20 µm). The PDMS prepolymer solution containing a mixture of 10:1 mass ratio of PDMS oligomers and reticular agent from Sylgard 184 Kit (Dow Corning, Wilmington, Del.) was then moulded against the silicon master. An anti-adhesive treatment of the master was priorly carried out using silanization in liquid phase with octadecyltricholorosilane (OTS) in order to enable easy demoulding of the polymer replica after thermal curing. PDMS was cured at a temperature of 80° C. for 2 hours. Once demoulded, the PDMS substrate was carefully cut into 1.8 cm×1.4 cm stamps. Next, to conduct the directed capillary assembly, we use a dedicated setup. The resulting PDMS stamp where we want the chromatin fragments to be assembled is placed on a motorized translation stage below a fixed glass spreader at a distance of about 1 mm. The experiment is conducted at ambient temperature. The chromatin solution is injected between the glass and the substrate and the liquid contact line is then moved over the substrate at a finely adjusted and constant velocity of 20 µm/sec for the trapped chromatin fragments to be carefully stretched. The main parameters governing this process are the molecular concentration, the velocity of the translation stage, the contact angle at the liquid/substrate/vapor interface, and the evaporation rate of the solvent. In this physical process, the microwell acts as a wetting defect that temporarily pins the moving contact line. During this pinning time, the convective flux of molecules in solution nourishes the interface, the contact angle of the liquid front line locally decreases, and the assembly takes place selectively by capillarity at each well. Under stretching of the meniscus due to the motion of the stage, some elastic energy is stored. When this energy exceeds the pinning energy, the front line abruptly disrupts, simultaneously stretching the trapped molecules and fixing them in that position. The assembly is performed throughout the entire surface of the PDMS stamp of an approximate 1 $cm^2$ area (see FIG. 17). To transfer the formed chromatin arrays onto the analysis support, the PDMS stamp with assembled chromatin fragments is brought into contact with a (3-Aminopropyl)triethoxysilane (APTES)-coated cover slip for 2 min and then peeled away (FIG. 11). The chromatin array transfers were characterized under an inverted epifluorescence microscope (×100 oil immersion objective) from Olympus coupled to a 512×512 CCD camera (Photometrics). The samples were imaged under illumination at 475 nm (em. 535 nm), nm and 620 nm (em. 700 nm) accordingly with no detectable cross-excitation at any of the emission wavelengths. Images were combined using ImageJ software.

AFM Imaging.

AFM images of chromatin arrays on APTES-coated glass slides were obtained on a NanoScope IIIa (Digital Instruments) in tapping mode operated in air.

Results and Discussion

The experimental procedure is depicted in FIG. 11. Our methodology is a combination of soft-lithography and molecular stretching that allows controlling the number, positioning and stretching of the chromatin molecules by capillarity during the assembly process. The resulting array is then transferred onto the analysis support by simple contact between the elastomeric stamp and the support.

Figure 12:
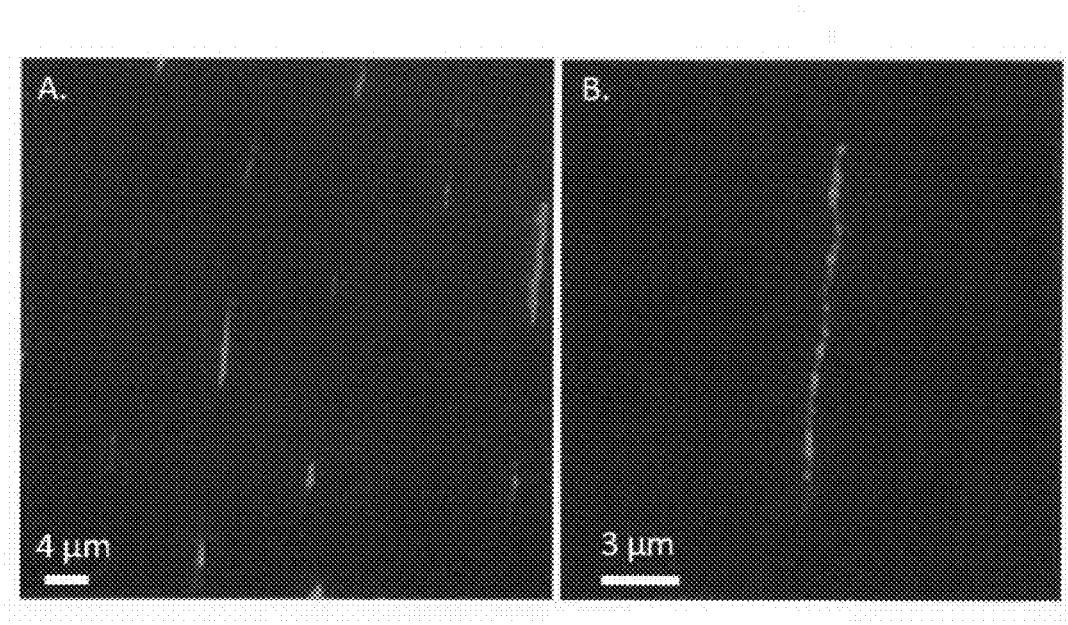
FIGS. 12A-12B are fluorescence images of an array of stretched and oriented M091 chromatin molecules transferred onto an APTES-coated cover slip (excitation at 475 nm). The molecules are YOYO-1 stained.
Figure 13:
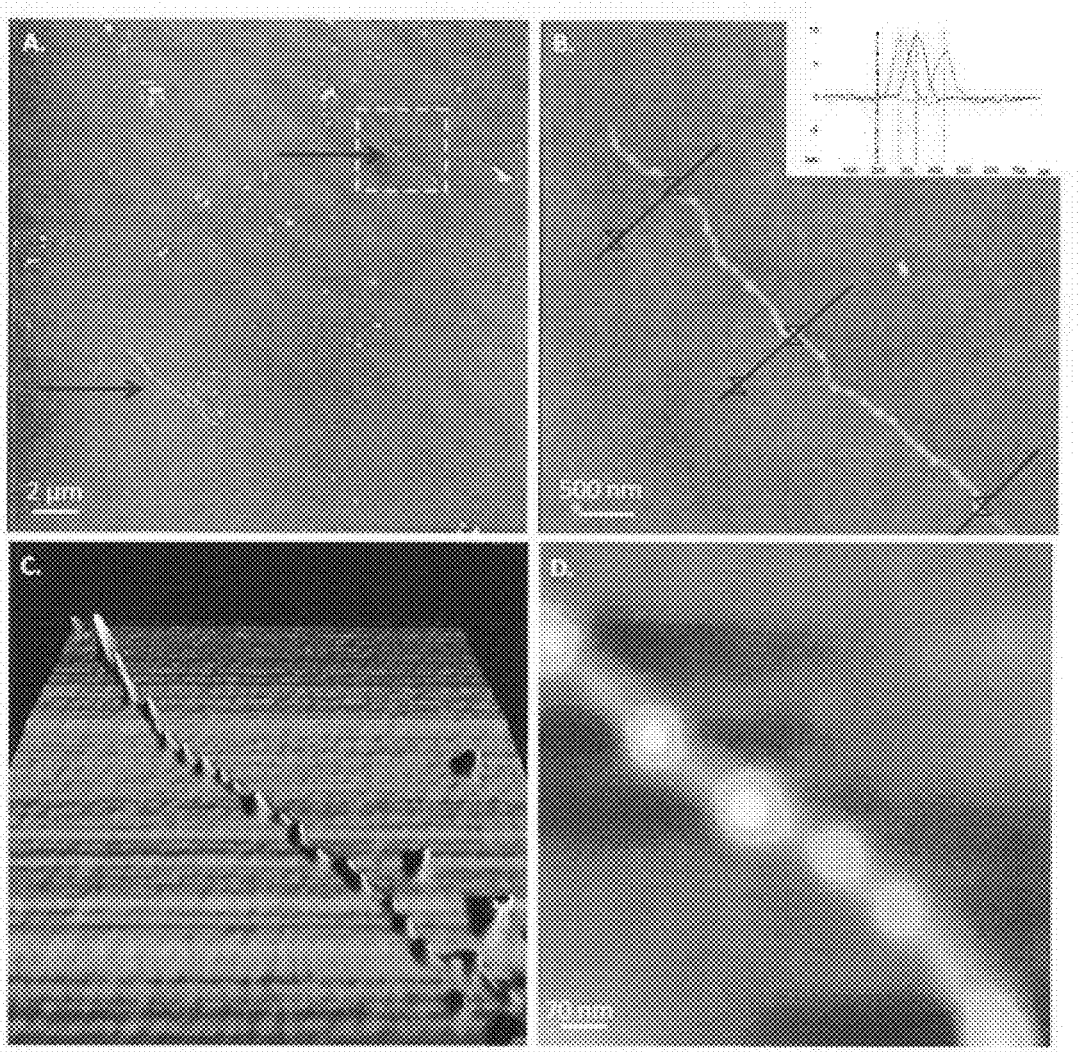
FIGS. 13A-13D illustrate AFM imaging of stretched and isolated chromatin molecule arrays.

We first focused our study on chromatin extracted from M091 cells. As a control experiment and to allow visualization of chromatin, DNA was stained with YOYO-1. FIGS. 12A-12B show the results obtained from directed capillary assembly of YOYO-1-stained M091 chromatin on a structured PDMS stamp and its subsequent transfer printing onto an APTES-coated cover slip through electrostatic interaction. The fluorescence images show that we obtain, after transfer, ordered and high density arrays of stretched and isolated fragments following a Poisson distribution and over large areas. The size distribution of the chromatin fragments ranges from about 5 kbp to 70 kbp, which corresponds to the expected lengths from the electrophoresis gel (see FIGS. 15A-15B).

The morphology of the stretched fragments appears to be different from the morphology of naked DNA (Gad et al., *J. Biomol. Struct. Dyn.* 2003, 2, 387-393; Luger et al., *Nature.* 1997, 389, 251-260). In some cases, we observe the presence of bright blobs along the molecules. We suggest these inhomogeneities could be caused by wrapping of stained DNA causing a local increase of fluorescence, uneven staining of DNA, a nod of nucleosomes, bent chromatin, or the presence of more than one fragment of chromatin. We used AFM imaging to confirm the chromatin structure and FIGS. 13A-13D show the obtained AFM images of the sample shown in FIGS. 12A-12B. We observe that the chromatin molecules we see in fluorescence, FIGS. 12A-12B, are decorated with complexes regularly spaced and evenly distributed along the entire fragments' length. The cross-section measurements indicate the average height of each complex to be 10.4±1.8 nm with 136.9±45.0 nm interdistance between adjacent ones. In between complexes, the height of linker DNA was measured at 1.76±0.38 nm. These values are consistent with the theoretical size of nucleosomes in mammalian chromatin which measure 10 nm in diameter in average (Bensimon et al., *Phys. Rev. Lett.* 1995, 74, 4754-4757) and are generally well organized despite cell heterogeneity. This suggests we are in the presence of individual nucleosomes across the fragments, further indicating that the technique allows the stretching of the chromatin fragments to a beads-on-a-string configuration. Note no cross-linking of chromatin molecules was required to fix the histones to the DNA in our process. As such, the forces exerted on the chromatin molecules during capillary assembly are difficult to compare with previous simulations that have been reported. On the one hand we find simulations of molecular combing on bare DNA molecules onto flat silanized or chemically functionalized surfaces (Malaquin et al., *Langmuir* 2007, 23, 11513-11521), but no simulations involving chromatin molecules to our knowledge. On the other hand, we find simulations on the pulling of chromatin molecules using optical traps or magnetic tweezers, where one end of the molecule is chemically modified so it attaches to the support and the other one is attached to a dielectric or paramagnetic bead through a biotin/streptavidin linkage and subjected to a traction or torsion force (Gorman et al., *Nat. Struct. Mol. Biol.* 2010, 17, 932-938; Streng et al., *Lab on a Chip.* 2009, 9, 2772-2774). In both approaches, DNA is chemically attached from one end while leaving the other end loose and receptive to the stretching force. However, neither of these techniques directly applies to our situation where the molecule is not tethered at one end and neither involves the use of topographical structures of any sort. In our case, we believe there is no chemical attachment but rather that the force elastically stretches the molecule in the immediate vicinity of the meniscus, temporarily "gluing" it to the surface as the meniscus recedes. As such, the pattern geometry plays here an important role as the direction and magnitude of the capillary forces induced by the contact line pinning depend strongly on it (Bustamante et al., *Curr. Op. Struct. Biol.* 2000, 10, 279-285). From literature, we know that on a hydrophobic substrate, the force exerted by flow combing is on the order of ~160 pN (Malaquin et al., *Langmuir* 2007, 23, 11513-11521), and that overstretching and denaturation of naked DNA is observed beyond 150-300 pN depending on sequence (Flors et al., *Current Op. Chem. Biol.* 2011, 15, 1-7). But are the elastic properties of chromatin comparable to the elastic properties of bare DNA? Optical trapping is one of the few techniques that have been able to provide insights into nucleosome dynamics. We know that trapping forces typically range between 0.1 and 100 pN, making this technique suited for investigation in the range of 0.01 and 10 pN (Flors et al., *Current Op. Chem. Biol.* 2011, 15, 1-7). Based on the work of Wang et al. (Wang et al., "Microfluidic Extraction and Stretching of Chromosomal DNA from Single Cell Nuclei for DNA Fluorescence In Situ Hybridization," *Biomed. Microdevices.* 2012, in press), we also know that the pulling force required to strip off nucleosomes from chromatin is on the order of tens of pN. Our method differs from molecular combing, and some key variants make the overall stretching force difficult to evaluate. In our experiment, the forces involved are an overall combination of various contributions (Van der Waals forces, hydrodynamic forces, substrate displacement, capillary force, convective flow, hydrophobic interactions). What we observe, however, is that the pinning of the molecules provides them with same alignment and orientation, that the resulting lengths are comparable to the lengths expected from the electrophoresis gels, and finally, that the nucleosomes are preserved during the process with interdistances kept constant and consistent with theory. These observations suggest that the forces exerted upon the fragments during the capillary assembly process are low enough to prevent the stripping of histones but at the same time high enough to allow the stretching of the fragments into the beads-on-a-string conformation necessary for high-resolution analysis. Thus, we can infer that with our substrate design and experimental parameters with a stage displacement speed of 20 µm/sec, the overall force is somewhat comprised between a few pN to a 100 pN. This ability to isolate individual chromatin fragments from an initial compacted higher-order form in solution refined into a beads-on-a-string conformation without the need for cross-linking is a characteristic of our technique which is essential for subsequent analysis. It gives access and insights into the entire library of information contained within individual chromatin fragments while preserving their native structure.

Figure 14:
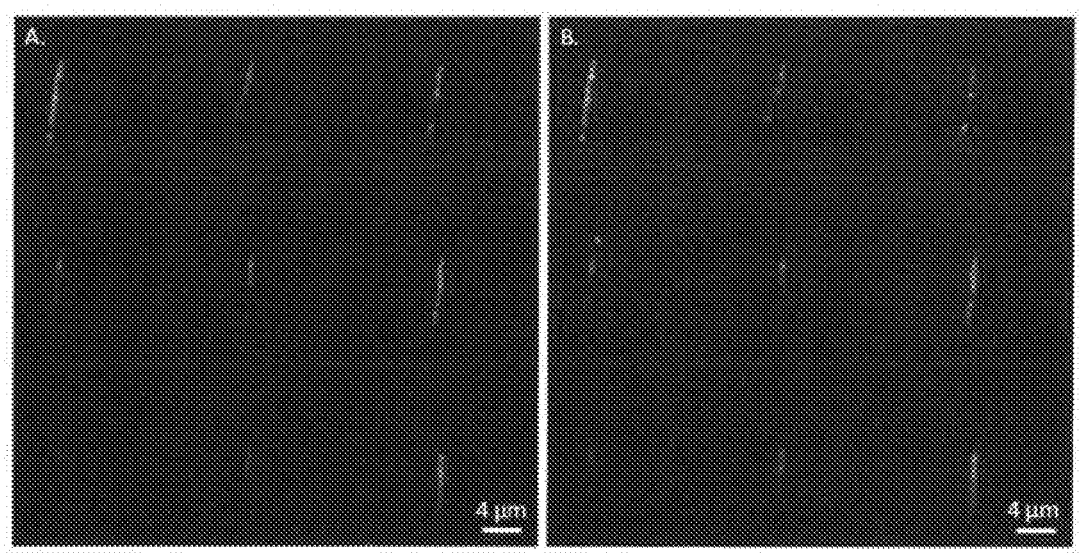
FIGS. 14A-14B show fluorescence micrographs of M091 chromatin fragments labeled with Alexa647-labeled histone H3 probes. DNA is stained with YOYO-1.
Figure 16:
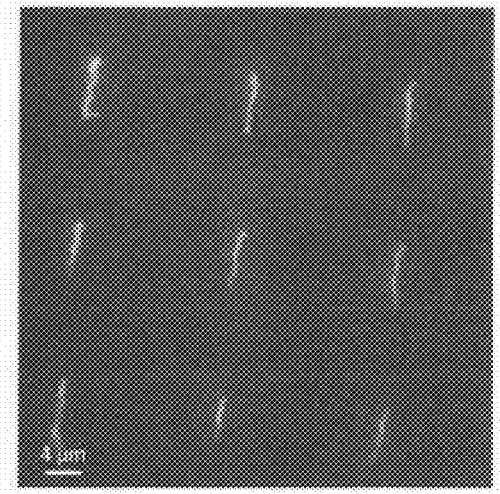
FIG. 16 is an overlay fluorescence image of an array of YOYO-1 stained M091 chromatin molecules incubated against Alexa 647 secondary antibodies. The image is the resulting overlay of the image taken at 475 nm excitation and the image taken at 620 nm excitation from the same area of the sample.

To confirm the preservation of native chromatin fragments, we interrogated the extracted chromatin fragments from M091 cells with histone H3 labels. For histone labeling, we used immunolabeling through specific recognition between a histone primary antibody and its corresponding fluorescently labeled secondary antibody. To validate the specificity of our labels, we first conducted several control experiments where only fluorescent secondary antibodies were incubated against chromatin, without any primary histone antibody intermediate. The results showed a very low rate of non-specific binding compared to the specific binding of histone antibodies of interest (FIG. 16). In fact, since the process takes place on a hydrophobic substrate (PDMS) and since the assembly only acts on the long-chain polymer strands, this method inherently washes away unbound or free-dyes and other contaminants. Consequently, no prior purification or washing steps are required. The specificity of the antibodies being validated, we repeated the experiments but this time using the specific probes of interest. The results from our chromatin immunolabeling are shown in FIGS. 14A-14B. The density of molecules in the arrays allows for histone distribution to be statistically compared across each sample and in-between different samples. We observe in FIG. 14B that, as expected from our AFM imaging, Alexa647-labeled H3 histone antibodies (shown in false-red color) are colocalized with the molecules and densely distributed across the entire length of the molecules. We notice that some fluorescent spots are brighter than others. These inhomogeneities that were already observed in FIGS. 12A-12B could also be caused here by the presence of protein aggregates at some locations across the stretched molecules. This experimental protocol was repeated with chromatin extracted from HeLa cells. As shown by the electrophoresis gel (FIGS. 15A-15B), the chromatin extraction from HeLa cells required lower micrococcal nuclease concentration and shorter digestion times to provide us with equivalent fragment sizes. Conversely, the experimental parameters used for stretching and generation of the HeLa chromatin arrays were kept identical, and similar results were obtained (see FIG. 17).

Considering the number of chromatin fragments per chip and the average length of the fragments, a simple calculation allows us to roughly estimate we could have about a human genome amount of DNA per chip. This suggests our technique would allow the imaging of an entire genome in a single experiment through a fast optical readout.

For data to be biologically relevant, the precision has to be at least one gene, or about 10,000 basepairs (bp). This implies that given the diffraction limit of optical microscopy of about 300 nm, chromatin has to be stretched to at least 30 bp/nm. If we analyze the panel of fluorescent images in FIGS. 14A-14B, the signals, even from the two closest probes of a 1 kbp separation distance are clearly discernible (FIGS. 14A-14B, the mean space measured between the two signals is 320 nm), from which we can conclude the resolution of our technique to be at least within 320 nm in fluorescence. However, this resolution can be easily increased by coupling fluorescence analysis with a nanometer-resolution technique such as AFM. Furthermore, as this methodology can be applied to various hydrophilic supports, this resolution could be further improved by using high-resolution fluorescence microscopy techniques such as Total Internal Reflection Fluorescence (TIRF), Photoactivated Localization Microscopy (PALM), or Stochastic Optical Reconstruction Microscopy (STORM) (Scandura et al., *PNAS.* 2004, 101, 15231-15236). It is not unreasonable to extrapolate that the fundamental principles outlined in our technique may permit molecular mapping and analysis with sufficient spatial resolution to identify multiple epigenetic marks on a single nucleosome or to distinguish marks on adjacent nucleosomes in native chromatin. Additionally, we could also envision coupling this chromatin array chip with optical tweezers for high-throughput native chromatin assays.

Conclusions

In summary, we have demonstrated a methodology to stretch and immobilize single native chromatin fragments derived from a mammalian genome, into a beads-on-a-string conformation. Our technique allows controlling the stretching factor of chromatin molecules to prevent stripping of histones from the molecules. We proved the applicability of this method by employing it in the case of two different cancerous cell types (M091 and HeLa). Thus, this procedure could be transposed, by extension, to other mammalian or non mammalian cell types of interest (embryonic stem cells, *drosophila* for example). This ability to controllably pattern large numbers of chromatin molecules over mm$^2$ areas offers the opportunity for parallelized and high-throughput screening with high-resolution capabilities. Therefore, chromatin mapping represents a powerful technique with the potential to serve as the basis of a FISH-like technique providing single molecule maps of multiple epigenetic features and their relation to a specific gene for single cell diagnostics. This technique could be extended to the use of microfluidics for dealing with material extracted from a single cell (Tegenfeldt et al., *PNAS.* 2004, 101, 10979-10983).

In addition to research studies, this affordable and fast technique may prove to be especially well-tailored for clinical settings as the procedure is straightforward and does not require complex fabrication or preparation protocols. In the imminent future, the need will arise to investigate the relationships between genetic and epigenetic marks not only within localized regions on the genome, but also among different cell types. This may grant new insight into the relation between chromatin structure and mechanisms of gene regulation during cellular differentiation and development as a means of bringing hope to tomorrow's medical treatment options and diagnostics.

Electrophoresis gels and control experiments were included as supporting information, along with videos, and fluorescence and AFM images obtained with chromatin extracted from HeLa cells (see FIGS. 15-19).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of high resolution imaging and analysis of native chromatin, said method comprising:
   (a) providing a plurality of native chromatin fragments;
   (b) immobilizing the plurality of native chromatin fragments to a transfer platform in an orderly pattern suitable for high resolution imaging of the plurality of native chromatin fragments, wherein said native chromatin fragments comprise both DNA and histones; and
   (c) conducting high resolution imaging and analysis of the native chromatin fragments,
   wherein the step (b) of immobilizing the plurality of native chromatin fragments to the transfer platform comprises the steps of:
   (i) providing a plurality of elongated individual native chromatin fragments removably coupled to a hydrophobic component in an orderly pattern suitable for high resolution imaging of the plurality of native chromatin fragments, wherein said native chromatin fragments comprise both DNA and histones; and
   (ii) transferring the plurality of elongated individual native chromatin fragments to a transfer platform, thereby yielding a chromatin array comprising the plurality of elongated individual chromatin fragments attached to the transfer platform in said orderly pattern,
   wherein said transfer platform comprises a support and a transfer surface layered on the support;
   wherein said transfer platform is effective to receive and capture the plurality of elongated individual chromatin fragments in said orderly pattern from said hydrophobic component; and
   wherein the native chromatin fragments are labeled with more than one different type of label for imaging or assaying purposes.

2. The method according to claim 1, wherein said hydrophobic component comprises a micro/nanostructured capture array comprising a hydrophobic surface having topographical features effective to assist in capillary-based trapping and elongation of individual native chromatin fragments in an orderly pattern.

3. The method according to claim 1, wherein the labeling comprises either bulk labeling of the native chromatin fragments prior to transferring them to the transfer platform or direct labeling of the native chromatin fragments after transferring them to the transfer platform.

4. The method according to claim 1, wherein the DNA is labeled, the histones are labeled, or both the DNA and histones are labeled.

5. The method according to claim 1, wherein said transfer surface is hydrophobic.

6. The method according to claim 5, wherein the hydrophobic transfer surface is selected from the group consisting of graphene, a graphene blend, a graphene derivative, a graphene-like compound, a thermoplastic, polycarbonate, vinyl, a silanized surface, an elastomer such as polydimethylsiloxane, a metal, a plastic, molybdenum, silicon, silicon nitride, copper, gold, and carbon.

7. The method according to claim 5, wherein the plurality of elongated individual native chromatin fragments are transferred to the transfer platform using solvent mediation.

8. The method according to claim 1, wherein said transfer surface is hydrophilic or is functionalized to have a hydrophilic surface.

9. The method according to claim 8, wherein the hydrophilic transfer surface or functionalized hydrophilic surface thereof is selected from the group consisting of silicon, silicon dioxide ($SiO_2$), glass, mica, a surface functionalized with hydrophilic functional groups, quartz, a silanized surface, and a surface functionalized with hydroxyl groups.

10. The method according to claim 1, wherein said high resolution imaging comprises techniques selected from the group consisting of optical imaging, optical tweezers technology, fluorescence microscopy, scanning probe microscopy, transmission electron microscopy (TEM), scanning transmission electron microscopy (STEM), electron energy loss spectroscopy (EELS), scanning electron microscopy (SEM), electron tomography, energy-filtered transmission electron microscopy (EFTEM), X-ray spectroscopy, and Auger electron spectroscopy.

11. The method according to claim 1, wherein said chromatin is from a source selected from the group consisting of a human, a non-human mammal, and a non-mammal.

12. The method according to claim 1, wherein the elongated chromatin fragments have a length of between about 5 kbp and about 100 kbp and are extended to their contour lengths.

13. The method according to claim 1, wherein the plurality of immobilized native chromatin fragments are labeled in bulk prior to being immobilized on the transfer platform or labeled individually after being immobilized on the transfer platform.

14. The array according to claim 1, wherein said native chromatin fragments are coupled to the transfer surface in a beads-on-a-string conformation.

* * * * *